United States Patent [19]
Mastalerz et al.

[11] Patent Number: 6,017,935
[45] Date of Patent: Jan. 25, 2000

[54] 7-SULFUR SUBSTITUTED PACLITAXELS

[75] Inventors: Harold Mastalerz, Guilford; John F. Kadow, Wallingford, both of Conn.

[73] Assignee: Bristol-Myers Squibb Company, Princeton, N.J.

[21] Appl. No.: 09/059,824

[22] Filed: Apr. 14, 1998

Related U.S. Application Data

[60] Provisional application No. 60/044,556, Apr. 24, 1997.

[51] Int. Cl.$^7$ ...................... A61K 31/335; C07D 265/30; C07D 295/02; C07D 305/14
[52] U.S. Cl. .......................... 514/337; 514/255; 514/319; 514/444; 514/449; 514/461; 514/232.8; 544/107; 544/374; 546/196; 548/525; 549/41; 549/60; 549/511
[58] Field of Search ................................ 514/232.8, 255, 514/319, 337, 428, 444, 449, 461; 544/107, 374; 546/196, 281.7; 548/525; 549/41, 60, 473, 511

[56] References Cited

U.S. PATENT DOCUMENTS

| | | |
|---|---|---|
| 4,814,470 | 3/1989 | Colin et al. . |
| 4,960,790 | 10/1990 | Stella et al. . |
| 5,175,315 | 12/1992 | Holton . |
| 5,227,400 | 7/1993 | Holton et al. . |
| 5,229,526 | 7/1993 | Holton . |
| 5,243,045 | 9/1993 | Holton et al. . |
| 5,254,580 | 10/1993 | Chen et al. . |
| 5,272,171 | 12/1993 | Ueda et al. . |
| 5,274,124 | 12/1993 | Holton . |
| 5,294,637 | 3/1994 | Chen et al. . |
| 5,336,785 | 8/1994 | Holton . |
| 5,352,806 | 10/1994 | Gunawardana et al. . |
| 5,466,834 | 11/1995 | Holton . |

FOREIGN PATENT DOCUMENTS

| | | |
|---|---|---|
| 590267A2 | 4/1994 | European Pat. Off. . |
| 600517A1 | 6/1994 | European Pat. Off. . |
| 764643A1 | 3/1997 | European Pat. Off. . |
| WO93/06093 | 4/1993 | WIPO . |
| WO94/08984 | 4/1994 | WIPO . |
| WO 94/13655 | 6/1994 | WIPO . |
| WO94/14787 | 7/1994 | WIPO . |
| WO94/20485 | 9/1994 | WIPO . |
| WO94/29288 | 12/1994 | WIPO . |
| WO96/03394 | 2/1996 | WIPO . |

OTHER PUBLICATIONS

E. K. Rowinsky and R. C. Donehower, "The Clinical Pharmacology and Use of Antimicrotubule Agents in Cancer Chemotherapeutics," Pharmac. Ther., 52: 35–84, 1991.

C. M. Spencer and D. Faulds, "Paclitaxel, A Review of its Pharmacodynamic and Pharmacokinetic Properties and Therapeutic Potential in the Treatment of Cancer," Drugs, 48(5), 794–847, 1994.

K.C. Nicolaou, et al, "Chemistry and Biology of Taxol," Angew. Chem., Int. Ed. Engl., 33: 15–44, 1994.

F.A. Holmes, et al, Taxane Anticancer Agents Basic Science and Current Status, edited by G.I. Georg, et al, 1995, American Chemical Society, Washington, D.C. 31–57.

S.G. Arbuck, et al, Taxol: Science and Applications, edited by M. Suffness, 1995 (CRC Press Inc., Boca Raton, Florida), pp. 379–415.

R.A. Johnson, "Taxol Chemistry. 7–O–Triflates as Precursors to Olefins and Cyclopropanes," Tetrahedron Letters, vol. 35, No. 43, pp. 7893–7896, 1994.

N. F. Magri, et al, "Modified Taxols 3. Preparation and Acylation of Baccatin III," J. Org. Chem., 51, pp. 3239–3242, 1986.

X. Liang and G.I. Kingston, "Synthesis and Biological Evaluation of Paclitaxel Analogs Modified in Ring C," Tetrahedron Letters, vol. 36, No. 17, pp. 2901–2904, 1995.

G. Roth, et al, "Reaction of Paclitaxel and 10–Desacetyl Baccatin III with Diethylamino Sulfurtrifluoride," Tetrahedron Letters, vol. 36, No. 10, pp. 1609–1612, 1995.

S.–H. Chen, et al, "The Chemistry of Taxanes: Reaction of Taxol and Baccatin Derivatives with Lewis Acids in Aprotic and Protic Media," Tetrahedron, vol. 49, No. 14, pp. 2805–2828, 1993.

L.L. Klein, "Synthesis of 9–Dihydrotaxol: A Novel Bioactive Taxane," Tetrahedron Letters, vol. 34, No. 13, pp. 2047–2050, 1993.

G. I. Georg, et al, "Stereoselective Synthesis of 9β–Hydroxytaxanes Via Reduction With Samarium Diiodide," Tetrahedron Letters, 36(11), pp. 1783–1786, 1995.

T.L. Riss, et al, "Comparison of MTT, XTT, and a Novel Tetrazolium Compound MTS for In–Vitro Proliferation and Chemosensitivity Assays," Mol. Biol. Cell 3 (Suppl.), 184a, 1992 (Abstract).

Physician's Desk Reference, 49th Edition, Medical Economics, p. 682, 1995.

*Primary Examiner*—Joseph K. McKane
*Assistant Examiner*—Taofiq A. Solola
*Attorney, Agent, or Firm*—Samuel J. DuBoff

[57] ABSTRACT

The present invention relates to novel taxane derivatives wherein, the taxol ring is substituted by sulfur groups on the C-7, their use as antitumor agents and pharmaceutical formulations.

19 Claims, No Drawings

7-SULFUR SUBSTITUTED PACLITAXELS

This application claims the benefit of Prov. Appln. No. 60/044,556 Apr. 24, 1997.

BACKGROUND OF THE INVENTION

1. Field of the Invention

The present invention concerns antitumor compounds. More particularly, the invention provides novel paclitaxel derivatives, pharmaceutical formulations thereof, and their use as antitumor agents.

2. Background Art

Taxol® (paclitaxel) is a natural product extracted from the back of Pacific yew trees, *Taxus brevifolia*. It has been shown to have excellent antitumor activity in in vivo animal models, and recent studies have elucidated its unique mode of action, which involves abnormal polymerization of tubulin and disruption of mitosis. It has recently been approved for the treatment of refractory advanced ovarian cancer and breast cancer; and studies involving other cancers have shown promising results. The results of paclitaxel clinical studies are reviewed by numerous authors, such as by Rowinsky and Donehower in "The Clinical Pharmacology and Use of Antimicrotubule Agents in Cancer Chemotherapeutices," *Pharmac. Ther.*, 52:35–84, 1991; by Spencer and Faulds in "Paclitaxel, A Review of its Pharmacodynamic and Pharmacokinetic Properties and Therapeutic Potential in the Treatment of Cancer," *Drugs*, 48 (5) 794–847, 1994; by K. C. Nicolaou et al. in "Chemistry and Biology of Taxol," *Angew. Chem., Int. Ed. Engl.* 33: 15–44, 1994; by F. A. Holmes, A. P. Kudelka, J. J. Kavanaugh, M. H. Huber, J. A. Ajani, V. Valero in the book "Taxane Anticancer Agents Basic Science and Current Status" edited by Gunda I. Georg, Thomas T. Chen, Iwao Ojima, and Dolotrai M. Vyas, 1995, American Chemical Society, Washington, DC, 31–57; by Susan G. Arbuck and Barbara Blaylock in the book "TAXOL® Science and Applications" edited by Mathew Suffness, 1995, CRC Press Inc., Boca Raton, Fla., 379–416; and also in the references cited therein.

A semi-synthetic analog of paclitaxel named Taxotere® (docetaxel) has also has been found to have good antitumor activity. The structures of paclitaxel and Taxotere® are shown below along with the conventional numbering system for molecules belonging to the class; such numbering system is also employed in this application.

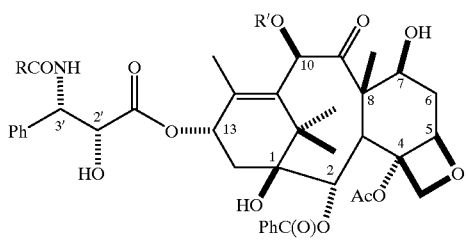

Taxol®: R=Ph; R'=acetyl
Taxotere®: R=t-butoxy; R'=hydrogen

SUMMARY OF THE INVENTION

This invention relates to novel antitumor compounds represented by formula I, or pharmaceutically acceptable salts thereof

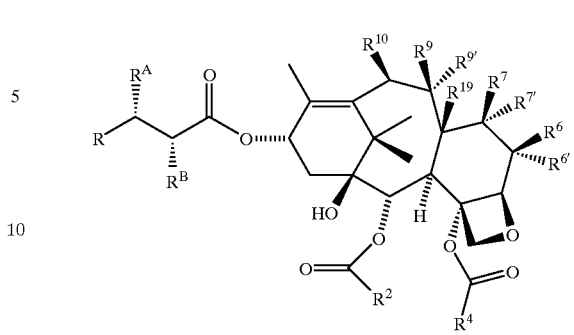

wherein R is hydrogen, $C_{1-6}$ alkyl, $C_{2-6}$ alkenyl, $C_{2-6}$ alkynyl, or $-Z^1-R^3$;

$Z^1$ is a direct bond, $C_{1-6}$alkyl, or $-O-C_{1-6}$alkyl;

$R^3$ is aryl, substituted aryl, $C_{3-6}$ cycloalkyl, $C_{3-6}$ cycloalkenyl, cyclic 3–7 membered ring containing either one or two heteroatoms, or heteroaryl;

$R^A$ is $-NHC(O)R$, $-NHC(O)OR$, $-NHC(O)NHR$, $-NHC(O)N(R)_2$, $-NHS(O)_kR$, $-NHP(=O)(OR)_2$ or $-NHP=S(OR)_2$, where k is 1 or 2;

$R^B$ is hydroxy, fluoro, $-OC(OR)R^x$, $-OC(O)OR^x$, $OP(O)(OH)_2$, $OCH_2OP(O)(OH)_2$, $-OCH_2OCH_2OP(=O)(OH)_2$, $OP(O)(OH)_2$ base, $OCH_2OP(O)(OH)_2$ base, $-OCH_2OCH_2OP(=O)(OH)_2$ base, $-(OCH)_2)$ $_mOC=OCH_2NHR^x$, $-(OCH_2)_mOC(=O)CH(R")NR'_6R'_7$ where m is 0–3, $-OCOCH_2CH_2NH_3^+HCOO^-$, $-OCOCH_2CH_2COOH$, $-OCO(CH_2)_3COOH$, $-OC(O)(CH_2)_nNR^FR^G$, where n is 0–3, $-OC(O)CH_2CH_2C(O)OCH_2CH_2OH$ or $-OC(O)-Z-C(O)-R'$;

Z is ethylene $(-CH_2CH_2-)$, propylene $(-CH_2CH_2CH_2-)$, $-CH=CH-$, 1,2-cyclohexane or 1,2-phenylene;

R' is $-OH$, $-OH$ base, $-NR'_2R'_3$, $-OR'_3$, $-SR'_3$, or $-OCH_2C(O)NR'_4R'_5$;

$R'_2$ is $-H$ or $-CH_3$;

$R'_3$ is $-(CH_2)_jNR'_6R'_7$ or $(CH_2)_nN^+R'_6R'_7R'_8X^-$, where j is 1–3;

$R'_4$ is $-H$ or $-C_1-C_4$ alkyl;

$R'_5$ is $-H$, $-C_1-C_4$ alkyl, benzyl, hydroxyethyl, $-CH_2CO_2H$ or dimethylaminoethyl;

$R'_6$ and $R'_7$ are independently $-H$, $-CH_3$, $-CH_2CH_3$, benzyl or $R'_6$ and $R'_7$ together with the nitrogen of $NR'_6R'_7$ form a pyrrolidino, piperidino, morpholino, or N-methylpiperizino group;

$R'_8$ is $-CH_3$, $-CH_2CH_3$ or benzyl;

$X^-$ is halide; base is $NH_3$, $(HOC_2H_4)_3N$, $N(CH_3)_3$, $CH_3N(C_2H_4)_2NH$, $NH_2(CH_2)_6NH_2$, N-methylglucamine, NaOH or KOH;

$R^F$ and $R^G$ are independently $-H$ or $-C_1-C_3$ alkyl, or $R^F$ and $R^G$ taken together with the nitrogen of $NR^FR^G$ form a pyrrolidino, piperidino, morpholino or N-methylpiperizino groups;

R" is $-H$, $-CH_3$, $-CH_2CH(CH_3)_2$, $-CH(CH_3)CH_2CH_3$, $-CH(CH_3)_2$, $-CH_2$phenyl, $-(CH_2)_3NH_2$, $-(CH_2)_4NH_2$, $-CH_2CH_2COOH$, $-(CH_2)_3NHC(=NH)NH_2$, the residue of the amino acid proline, $-OC(O)CH=CH_2$, $-C(O)CH_2CH_2C(O)NHCH_2CH_2SO_3-Y+$ or $-OC(O)CH_2CH_2C(O)NHCH_2CH_2CH_2SO_3-Y+$;

Y+ is Na+ or N+(Bu)$_4$;

$R^2$ is aryl or substituted aryl;

$R^4$ is $-C_{1-6}$ alkyl, $-OC-C_{1-6}$ alkyl, or $-C_{3-6}$ cycloalkyl;

$R^6$ and $R^{6'}$ are independently hydrogen, hydroxy, $C_{1-6}$ alkyl, $-SH$, $-S-R^W$, halo, or together $R^6$ and $R^{6'}$ form a ketone;

$R^7$ and $R^{7'}$ are independently hydrogen, mercapto, —S—$R^W$, —S($R^W$)$_2$$^+$K$^-$, —S(O)—$R^W$, —S(O)$_2$$R^W$, —S(O)$_2$OH and the corresponding salts, —S(O)$_2$NHR$^x$, —S(O)$_2$N(R$^x$)$_2$, —S—S—$R^W$, —S—S—R$^3$, —S(CH$_2$)$_a$R$^3$, where a is 0–4, —S—CN, —S(O)—CN, —S(O)$_2$—CN, —SC(O)R$^x$, —SC(O)OR$^x$, —SC(S)R$^x$, —SC(S)SR$^x$, —SC(O)NHR$^x$, —SC(OH)NR'$_6$R'$_7$, —SCH$_2$OR, —SC(R$^x$)$_2$OR, —SCHR$^x$OR, —SCH$_2$OCH$_2$OCH$_3$, —SCH$_2$SR, —SC(R$^x$)$_2$SR, —SCHR$^x$SR, —SCOCH$_2$CH$_2$NH$_3$$^+$HCOO$^-$, —SCOCH$_2$CH$_2$COOH, —SCO(CH$_2$)$_3$COOH, —OC(O)(CH$_2$)$_n$NR$^F$R$^G$, where n is 0–3, —SC(O)—Z—C(O)—R', —SC(O)CH$_2$CH$_2$C(O)OCH$_2$CH$_2$OH, —S(O)$_b$CH$_2$CN, where is b is 0–2, —SCH$_2$C(O)C$_{1-6}$ alkyl, —SCH=C(X)(Y), —S(SCH$_2$)$_r$R$^2$, where r is 1–4, or —S(CH$_2$)S(O)$_t$C$_{1-6}$ alkyl, where t is 0–2, with the proviso that both of R$^7$ and R$^{7'}$ cannot simultaneously be hydrogen;

X and Y are independently hydrogen, COOR$^a$, C(O)R$^a$, R$^a$, CN, aryl or heteroaryl, where R$^a$ is C$_{1-6}$ alkyl;

K is Br$^-$, Cl$^-$, I$^-$, CH$_3$SO$_3$—, BF$_4$—, CF$_3$COO—, CH$_3$COO— or CF$_3$SO$_2$—;

R$^9$ and R$^{9'}$ are independently hydrogen or hydroxy or together R$^9$ and R$^{9'}$ form a ketone; provided R$^{9'}$ and R$^{7'}$ taken together can form part of a ring joined by —CH$_2$S(O)$_q$— in which the carbon is attached at R$^{9'}$ and the sulfur at R$^{7'}$ and where q is 0–2, R$^9$ is —OH, and R$^7$ is hydrogen; further provided R$^{9'}$ and R$^{7'}$ taken together can form part of a ring joined by =CHS(O)$_q$— in which the carbon is attached at R$^9$ and R$^{9'}$ to form a double bond and the sulfur at R$^{7'}$ and where q is 0–2, and R$^7$ is hydrogen;

R$^{10}$ is hydrogen, hydroxy, —OC(O)R$^x$, —OC(O)OR$^x$, —O—C$_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$—OCH$_2$OCH$_2$CH$_2$OH, —OCH$_2$SR, —OCH$_2$OCH$_2$SCH$_3$, —OC(O)NR'$_6$R'$_7$, C$_{1-6}$ alkyl, —(CH$_2$)$_3$C(O)R$^x$, —(CH$_2$)$_3$C(O)OR$^x$, —(CH$_2$)$_3$CN, —OP(O)(OH)$_2$, —OCH$_2$OP(O)(OH$_2$), —OCH$_2$OCH$_2$OP(O)(OH$_2$, —(OCH$_2$)$_n$OC=OCH$_2$NHR$^x$, —(OCH$_2$)$_n$OC(=O)CH$_{(R'')NR'6}$R'$_7$, where n is 0–3, —OCOCH$_2$CH$_2$NH$_3$$^+$HCOO$^+$, —OCOCH$_2$CH$_2$COOH, —OCO(CH$_2$)$_3$COOH, —OC(O)—Z—C(O)—R', —OC(O)(CH$_2$)$_n$NR$^F$R$^G$ where n is 0–3, or —OC(O)CH$_2$CH$_2$C(O)OCH$_2$CH$_2$OH;

R$^{19}$ is methyl or hydroxymethyl;

R$^x$ is C$_{1-6}$ alkyl, C$_{2-6}$ alkenyl, C$_{2-6}$ alkynyl, C$_{3-6}$ cycloalkyl any of which groups can be optionally substituted with one to six of the same or different halogen atoms or with one or more hydroxy groups; and R$^W$ is C$_{1-6}$ alkyl any of which groups can be optionally substituted with one to six of the same or different halogen atoms or with one or more hydroxy groups or with one or more carboxy groups or with one or more carboxy C$_{1-6}$ alkyl esters or with one or more mercapto groups.

Another aspect of the present invention provides a method for inhibiting tumor in a mammalian host which comprises administering to said mammalian host an antitumor effective amount of a compound of formula I.

Yet, another aspect of the present invention provides a pharmaceutical formulation which comprises an antitumor effective amount of a compound of formula I in combination with one or more pharmaceutically acceptable carriers, excipients, diluents or adjuvants.

Another aspect of the invention provides for novel baccatin intermediate compounds of the formula II

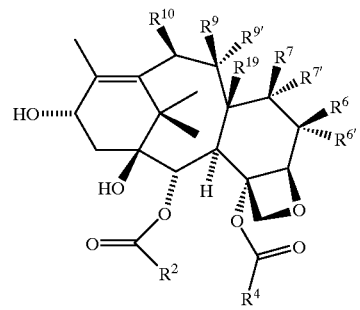

II

DETAILED DESCRIPTION

In the application, unless otherwise specified explicitly or in context, the following definitions apply. The numbers in the subscript after the symbol "C" define the number of carbon atoms a particular group can contain. For example "C$_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "C$_{1-6}$ alkyl" can also refer to C$_{1-6}$ alkenyl which bridges two groups; examples include propane-1,3-diyl, butane-1,4-diyl, 2-methyl-butane-1,4-diyl, etc. "C$_{2-6}$ alkenyl" means a straight or branched carbon chain having at least one carbon atoms; examples include bond, and having from two to six carbon atoms; examples include ethenyl, propenyl, isopropenyl, butenyl, isobutenyl, pentenyl, and hexenyl. Depending on the context, "C$_{2-6}$ alkenyl" can also refer to C$_{2-6}$ alkenydiyl which bridges two groups, examples include ethylene-1,2-diyl (vinylene), 2-methyl-2-butene-1,4-diyl, 2-hexene-1,6-diyl, etc. "C$_{2-6}$ alkynyl" means a straight or branched carbon chain having at least one carbon-carbon triple bond, and from two to six carbon atoms; examples include ethylnyl, propynyl, butynyl, and hexynyl.

"Aryl" means aromatic hydrocarbon having from six to ten carbon atoms; examples include phenyl and naphthyl. "Substituted aryl" means aryl independently substituted with one to five (but preferably one to three) groups selected from C$_{1-6}$ alkanoyloxy, hydroxy, halogen, C$_{1-6}$ alkyl, trifluoromethyl, C$_{1-6}$ alkoxy, aryl, C$_{2-6}$ alkenyl, C$_{1-6}$ alkanoyl, nitro, amino, cyano, azido, C$_{1-6}$ alkylamino, di-C$_{1-6}$ alkylamino, and amido. "Halogen" means fluorine, chlorine, bromine, and iodine.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

"Hydroxy protecting groups" include, but is not limited to, ethers such as methyl, t-butyl, benzyl p-methoxybenzyl, p-nitrobenzyl, allyl, trityl, methoxymethyl, methoxyethoxymethyl, ethoxyethyl, tetrahydropyranyl, tetrahydrothiopyranol, dialkylsilylethers, such as dimethyl-silyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, *Protective Groups in Organic Synthesis*, 2d Ed., 1991, John Wiley & Sons, and McOmie; and *Protective Groups in Organic Chemistry*, 1975, Plenum Press.

"Ph" means phenyl; "ipr" means isopropyl; "DAST" means diethylamino sulfur trifluoride.

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include for example, lower alkoxy such as methoxy, ethoxy, butoxy, halogen such as chloro or fluoro, nitro, amino, and keto.

A preferred embodiment are compounds I, or pharmaceutically acceptable salts thereof, wherein additionally:

R is 2-furanyl (2-furyl), 2-thienyl, 3-furanyl (3-furyl), 3-thienyl, phenyl, substituted phenyl, $C_{3-6}$ alkyl, $C_{3-6}$ alkenyl, $C_{3-6}$ cycloalkyl or $C_{3-6}$ cycloalkenyl;

$R^A$ is —NHC(O)Ph, wherein Ph is substituted or unsubstituted, —NHC(O)O($C_{1-6}$ alkyl), —NHC(O)OCH$_2$Ph, NHC(O)-heterocycle, —NHC(O)NHR or —NHC(O)N(R)$_2$;

Another preferred embodiment are compounds I, or pharmaceutically acceptable salts thereof, wherein additionally:

R is phenyl, mono or di-substituted phenyl, $C_{3-6}$ cycloalkyl, $C_{3-6}$ alkyl, $C_{3-6}$ alkenyl or $C_{3-6}$ cycloalkenyl;

$R^2$ is phenyl or substituted phenyl;

$R^B$ is hydroxy, —OC(O)R$^x$, —OC(O)OR$^x$, OP(O)(OH)$_2$, OCH$_2$OP(O)(OH)$_2$, —OCH$_2$OCH$_2$OP(=O)(OH)$_2$, OP(O)(OH)$_2$ base, (CH$_2$OP(O)(OH)$_2$ base, —OCH$_2$OCH$_2$OP(=O)(OH)$_2$ base, —(OCH$_2$)$_m$OC=OCH$_2$NHR$^x$, —(OCH$_2$)$_m$OC(=O)CH(R")NR'$_6$R'$_7$ where m is 0–3, —OCOCH$_2$CH$_2$NH$_3$$^+$HCOO$^-$, —OCOCH$_2$CH$_2$COOH, —OCO(CH$_2$)$_3$COOH, —OC(O)(CH$_2$)$_n$NR$^F$R$^G$, where n is 0–3, —OC(O)CH$_2$CH$_2$C(O)OCH$_2$CH$_2$OH or —OC(O)—Z—C(O)—R';

$R^{10}$ is hydrogen, hydroxy, —OC(O)R$^x$, —OC(O)OR$^x$, —O—C$_{1-6}$ alkyl or —OCH$_2$OCH$_3$;

The new products that have the general formula I display a significant inhibitory effect with regard to abnormal cell proliferation, and have therapeutic properties that make it possible to treat patients who have pathological conditions associated with an abnormal cell proliferation. The pathological conditions include the abnormal cellular proliferation of malignant or non-malignant cells in various tissues and/or organs, including, non-limitatively, muscle, bone and/or conjunctive tissues; the skin, brain, lungs and sexual organs; the lymphatic and/or renal system; mammary cells and/or blood cells; the liver, digestive system, and pancreas, and the thyroid and/or adrenal glands. These pathological conditions can also include psoriasis, solid tumors; ovarian, breast, brain, prostate, colon, stomach, kidney, and/or testicular cancer, Karposi's sarcoma; cholangiocarcinoma; choriocarcinoma; neuroblastoma; Wilm's tumor, Hodgkin's disease; melanomas; multiple myelomas; chronic lymphocytic leukemias; and acute or chronic granulocytic lympho mas. The novel products in accordance with the invention are particularly useful in the treatment of non-Hodgkin's lymphoma, multiple myeloma, melanoma, and ovarian, urothelial, oesophageal, lung, and breast cancers. The products in accordance with the invention can be utilized to prevent or delay the appearance or reappearance, or to treat these pathological conditions. In addition, the compounds of formula I are useful in treating and/or preventing polycystic kidney diseases (PKD) and rheumatoid arthritis.

The compounds of this invention can be made by techniques from the conventional organic chemistry repertoire. Schemes I–XIII, which depict processes that compounds within the scope of formula I can be made, are only shown for the purpose of illustration and are not to be construed as limiting the processes to make the compounds by any other methods.

The compounds I of this invention are 7-sulfur substituted taxane analogs. All of the contemplated analogs can be prepared from a previously reported 7-triflate intermediate (Scheme I) or suitably substituted analogs. The preparation of this intermediate is shown in Scheme I.

As shown in Scheme I, the starting material is a known taxane analog. The analog with an intact sidechain is suitably protected to leave the most reactive hydroxy group at C-7. Compound 1 in Scheme I is protected at the 2' hydroxy group at the sidechain. Step A describes the protection of the 2' hydroxy group as a 2' tertbutyldimethylsilyl ether. This protecting group is well known in the taxane art and has been described by several authors including Kingston and George. The example of compound 1 actually described utilizes this silyl protecting group at the 2' position. Although this group is preferred, other protecting groups can be utilized. The preparation of intermediate 1 are now well known in the art. The synthesis of the 7-trifluoromethanesulfonate (triflate) intermediate 2 is shown in step B and is by now well known in the art. The preparation of 7-O triflates and its conversion into cyclopropane and olefin has been divulged by Johnson, R. A., et al., *Taxol Chemistry. 7-O Triflates as precursors to olefins and cyclopropanes. Tetrahydron Letters*, 1994. 35(43); p. 7893–7986 & by the same authors in WO 94/29288. The preferred synthesis utilizes DMAP as the base and triflic anhydride as the activating agent.

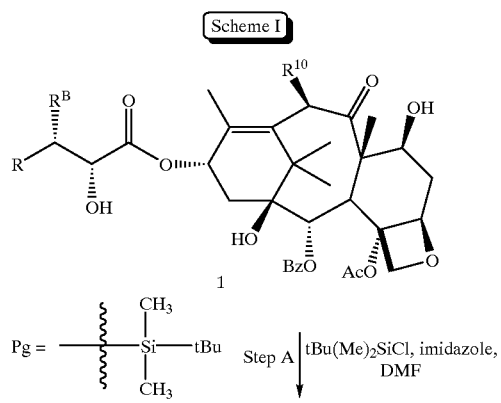

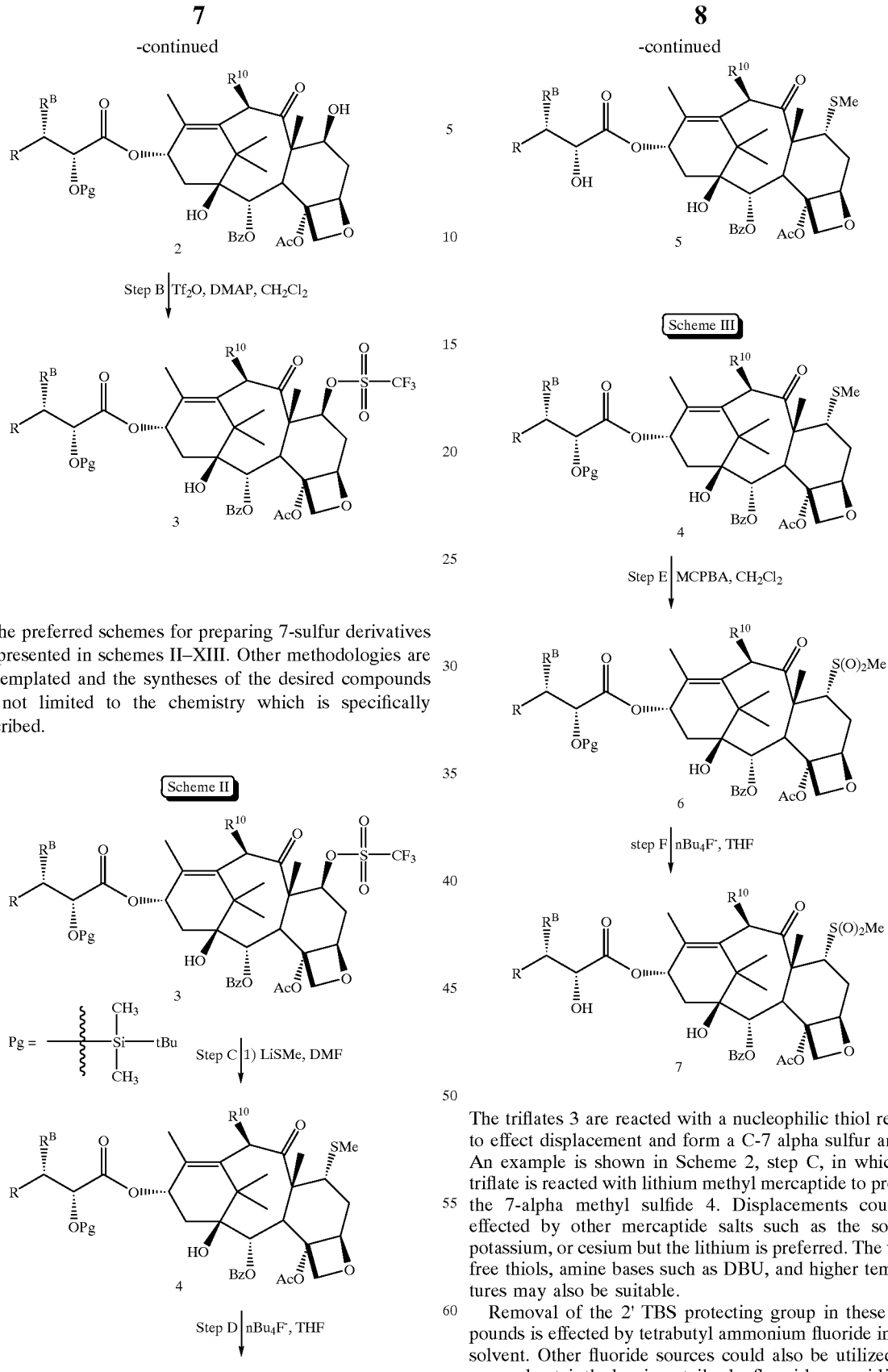

The preferred schemes for preparing 7-sulfur derivatives are presented in schemes II–XIII. Other methodologies are contemplated and the syntheses of the desired compounds are not limited to the chemistry which is specifically described.

The triflates 3 are reacted with a nucleophilic thiol reagent to effect displacement and form a C-7 alpha sulfur analog. An example is shown in Scheme 2, step C, in which the triflate is reacted with lithium methyl mercaptide to produce the 7-alpha methyl sulfide 4. Displacements could be effected by other mercaptide salts such as the sodium, potassium, or cesium but the lithium is preferred. The use of free thiols, amine bases such as DBU, and higher temperatures may also be suitable.

Removal of the 2' TBS protecting group in these compounds is effected by tetrabutyl ammonium fluoride in THF solvent. Other fluoride sources could also be utilized. For example triethylamine trihydrofluoride, pyridinium hydrofluoroide, potassium fluoride, or cesium fluoride may find utility. The potassium fluoride may be utilized in combination with a complexing agent such as 18-crown-6 or the like to aid in desilylation. A solvent such as acetonitrile is typically used under these conditions. Other conditions such as mild aqueous hydrochloric acid and a cosolvent such as acetonitrile or THF may be useful for deprotection. The same conditions work equally well for triethylsilyl or trimethylsilyl groups and are applicable for other silicon based protecting groups.

Many of the schemes refer to a hydroxy protecting group, preferably a trialkylsilyl group. It is to be understood that hydroxy protecting group may be a carbonate or ester group —C(O)OR$^x$ or —C(O)R$^x$ or substituted methyl or benzyl ethers. Thus when such a group is employed as a hydroxy protecting group, it may be removed to generate the free hydroxy protecting group. Many suitable protecting groups can be found in the book "Protective Groups in Organic Synthesis; 2nd ed. by Thedora W. Greene and Peter G. M. Wuts Copyright 1991 by John Wiley and Sons Inc."

The 2' protected sulfide intermediate 4 can be oxidized to the intermediate diasteromeric sulfoxides or sulfones. As shown in Scheme 3, step E, oxidation with 2 equivalents of a peracid such as MCPBA produces the sulfone 6, which can be subsequently be deprotected as described above to produce the sulfone 7. Utilization of sodium periodate in aqueous methanol solvent or 1 equivalent of MCPBA at low temperature such as −78° in step E would produce the corresponding sulfoxides rather than sulfone. Deprotection as described above would produce the 7-alpha methyl sulfoxide.

As shown in Scheme IV, deprotonation of the sulfone 6 with a strong amine base such as lithium bistrimethylsilylamide and subsequently quenching with a proton source such as aqueous ammonium chloride results in a cyclized product 8, the result of an addition to the C-9 ketone moiety. Deprotection of the 2' hydroxy group as described above for step D provided the fully deprotected compound 9.

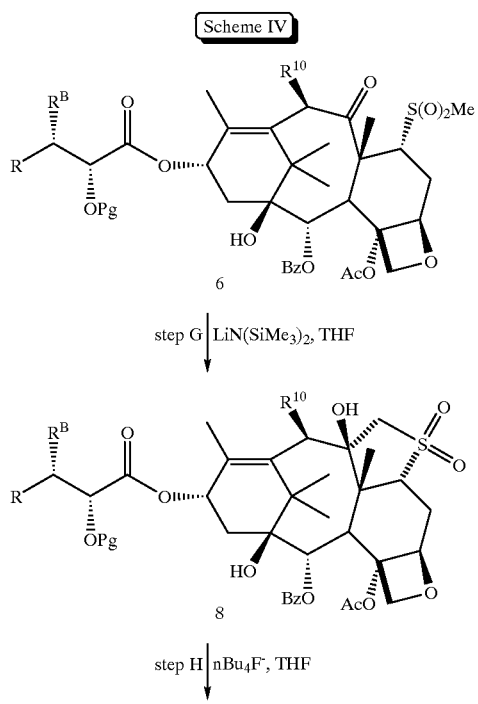

Scheme V describes the preparation of C-7 thioesters. Displacement of the triflate 3 with potassium thioacetate as shown in Step H produces the C-7 alpha thioester which is protected at the 2' hydroxy group. Other salts of the thioester or use of the thioacid with Mitsunobu conditions (triphenylphosphine, DEAD) could also be used to produce the same product. Deprotection using the conditions described in Step D above would produce the C-7-alpha thioester analog.

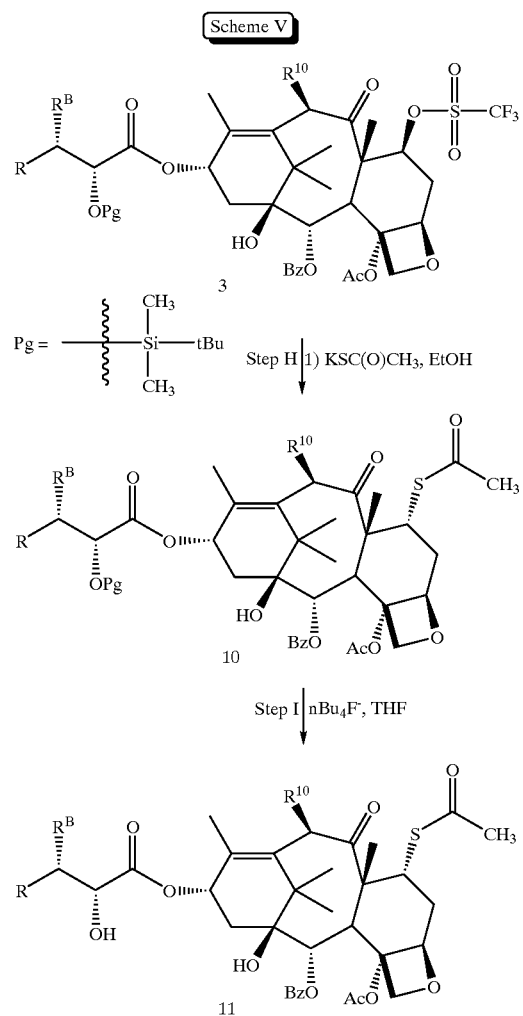

As shown in Scheme VI, Step J, the thioester 10, can be hydrolyzed using ethanolic ammonia to produce the C-7 alpha thiol substituted taxane 12. Epimerization of this thiol moiety as described in Step K produces a mixture of the C-7 beta thiol 13 and the starting material 12 in which the former predominates. Chromatographic separation provides pure 13. Deprotection as described above for Step D produces the beta thiol analog 14 (Scheme VII).

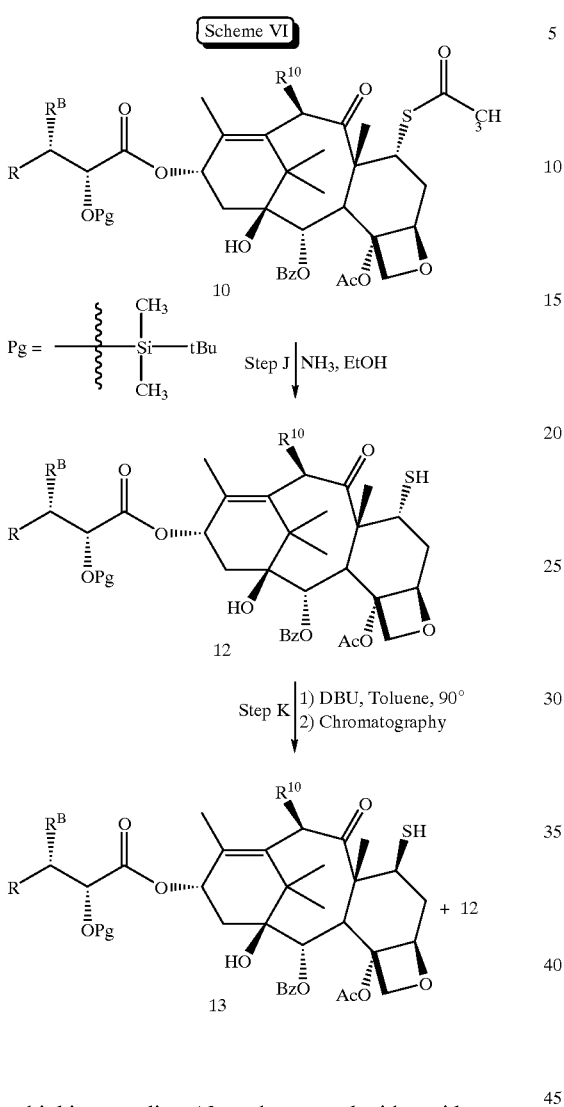

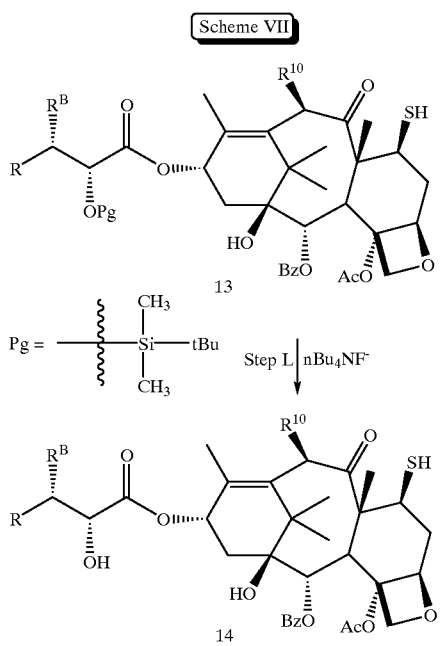

The thiol intermediate 13 can be reacted with a wide range of electrophilic reagents to produce the C-7 beta sulfur analogs described in this invention. As described in Scheme VIII, Step M, reaction of the thiol with bromomethyl ether or chloromethyl methyl ether in the presence of a base will produce the desired thioacetal 15. Amines bases in inert solvents such as dichloromethane, 1,2-dichloroethane, or toluene could be utilized. Typical amine bases include triethylamine, diisopropyl ethylamine, DMAP, or DBU. Alternatively stronger bases such as lithium (or sodium or potassium) bistrimethylsilylamide or LDA could be utilized typically in solvents such as THF, Dioxane, diethyl ether, or the like. A wide range of temperatures may be employed depending on the reagents and solvent combinations. Step N, the deprotection can be carried out as described above for Step D.

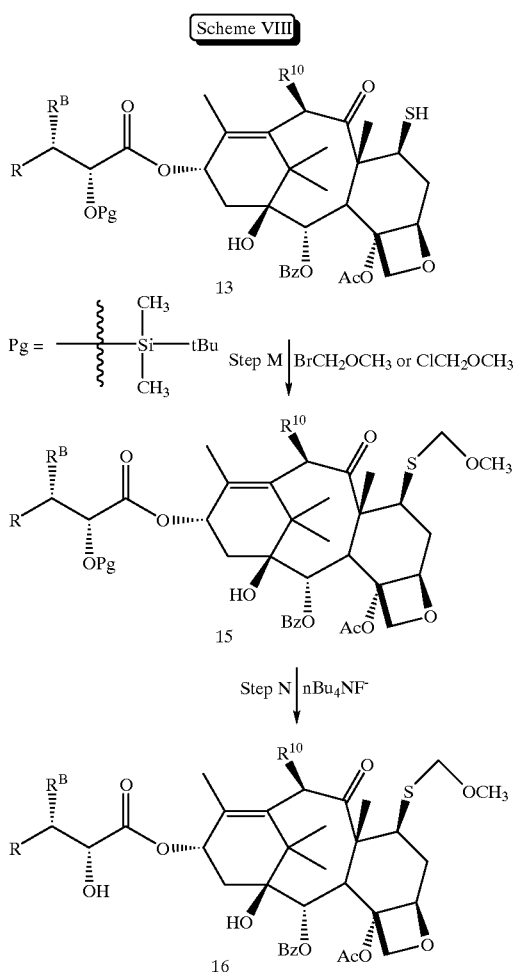

Scheme IX describes the methylation of thiol 13 in Step N in order to produce the methyl sulfide 17. Reaction with methyl iodide and DBU produces the methyl sulfide. Alternatively stronger bases or alternative amine bases could be used. Phase transfer methylation conditions using a methyl iodide, an aqueous base (NaOH, KOH), a phase transfer catalyst (suitable quaternary amine such as Adogen 454), and an inert solvent such as methylene chloride could be utilized. Other methylating agents such as dimethyl sulfate, methyl bromide, or methyl triflate could be utilized. This methodology could also be used with other aklylating reagents in order to produces sulfides with other than methyl groups. Deprotection as described in Step O (equivalent to Step D) above produces the methyl sulfide 18.

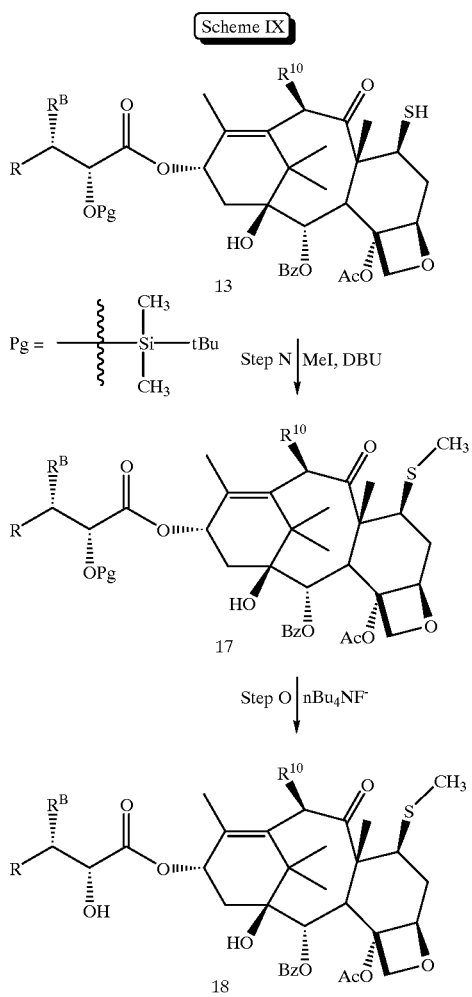

Another example of thiol alkylation is shown in Scheme X. Reaction of the thiol 13 in an inert solvent such as benezene with ethylene oxide in the presence of DBU produces the 7-beta-hydroxyethyl sulfide 19 which can be deprotected as described above in Step R (equivalent to Step D).

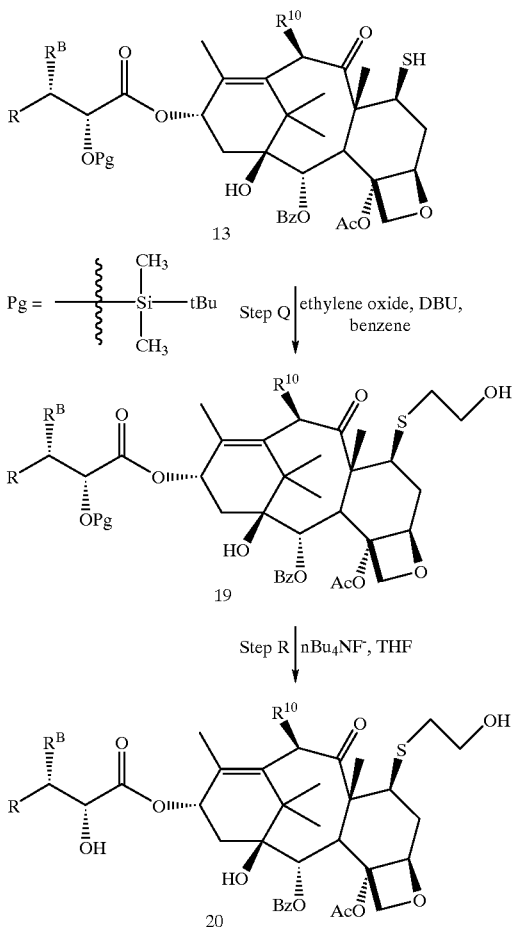

The examples supplied for the current invention describe analogs containing a β-phenyl isoserine C-13 sidechain which is the sidechain found in paclitaxel as well as analogs with alternative, modified sidechains. The entire sequences shown in the Schemes above could be carried out using a starting material 1 which already contains a modified sidechain.

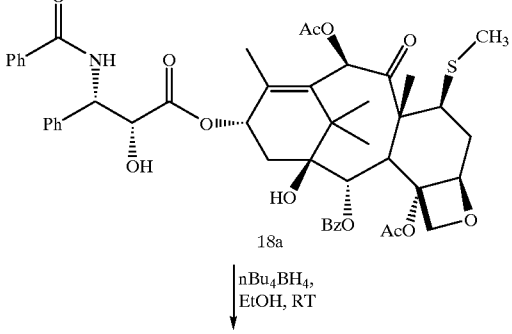

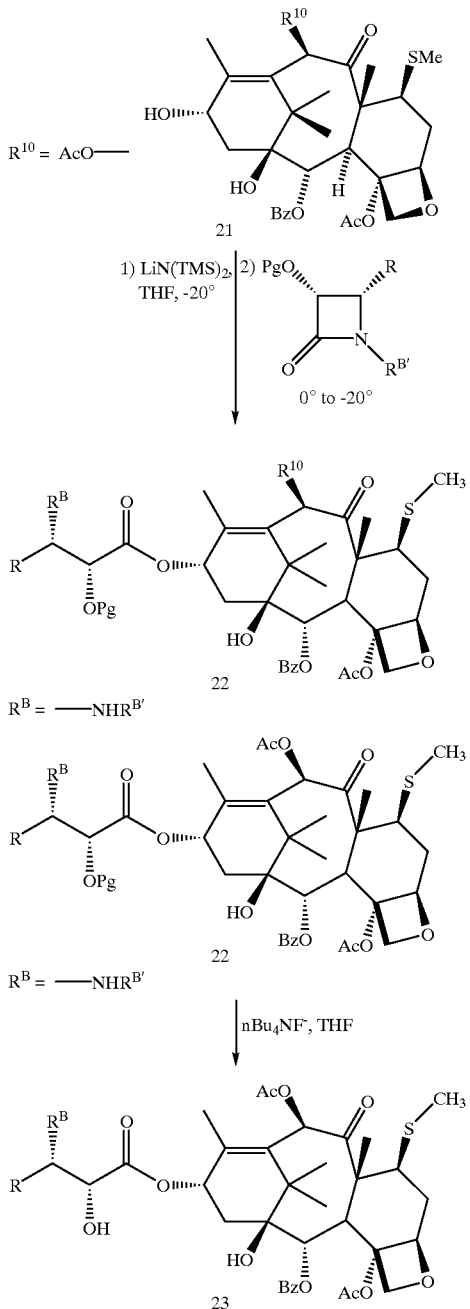

5,243,045; 5,227,400; 5,336,785) provides compound 22. Methods for preparing suitably substituted β-lactams can be found in U.S. Pat. No. 5,175,315, European patent application 0 590 267 A2, the other U.S. patents mentioned above, or references therein. Detailed examples of coupling substituted lactams to 7-substituted baccatin derivatives and the requisite references can be found in U.S. Pat. No. 5,254,480, U.S. Pat. No. 5,294,637, or EP 0 590 267 A2. Some example of using β-lactams to prepare other substituted taxane derivatives are in PCT WO/14787. This patent also describes an alternative methods for attaching substituted isoserine sidechains to substituted baccatins which would be applicable for the compounds of this invention. In compound 21, $R^{10}$ is acetoxy. In compounds where $R^{10}$ is hydroxy, a suitable protecting group must be utilized prior to sidechain cleavage or installed selectively on the C-10 hydroxy group prior to the coupling reaction. Trialkylsilyl, CBz, or Troc protecting groups are suitable for this protecting group step and can be attached using methodology which is well known in the art.

Finally, deprotection of the 2' protecting group as described previously in Step D provides the desired compounds 23 with a modified sidechain. The 2' protecting group is preferably trialkylsilyl but others work as also described in Step D above.

Scheme XII describes one synthesis of 7 vinyl sulfide taxane analogs which are covered by this invention. As shown in Step U, the mercapto taxane intermediate 13 is allowed to add to an appropriate vinyl sulfoxide to form an intermediate beta sulfur substituted sulfoxide. This intermediate 25 could be isolated but it is easier to heat the reaction mixture to effect sulfenic acid elimination and concomitant formation of Compound 26. This compound is then deprotected as previously described in Step D to provide the desired vinyl sulfide Compound 27. While this reaction may be carried out in any inert solvent, toluene or a higher boiling aromatic solvent such as xylene is preferred because the resulting intermediate may be directly heated without isolation to effect sulfoxide elimination and vinyl sulfide formation. DBU is the preferred base but other tertiary amine bases may also be utilized. As described for other schemes, alternate protecting groups of the 2' hydroxy group may be utilized but the tertbutyl dimethylsilyl moiety is the preferred one. Other substituted sulfoxides may be utilized to obtain substituted vinyl compounds. For example utilization of 1-methyl-phenyl vinyl sulfoxide would produce a vinyl sulfide with a methyl group on the 2 position of the olefin.

Alternatively, the paclitaxel sidechain could be cleaved and the resulting substituted baccatin analog reattached to a novel sidechain of choice. Scheme XI provides an example of such a sequence using the 7-methylthiomethyl analog 18a as the starting material. Reaction of 18a with tetrabutylammonium borohydride via the method of Magri et al. in J. Org. Chem. 1986, 51, pp.-3239–3242 provides the 7-sulfur substituted baccatin derivatives such as 21 (Scheme XI). For examples of the use of the Magri methodology to prepare other 7-substituted baccatins see U.S. Pat. No. 5,254,580 or U.S. Pat. No. 5,294,637. These baccatin derivatives can be reacylated by a new sidechain using any of the methodology already well known in the art. For example reaction of 21 with a suitably substituted lactam via the method of Holton (U.S. Pat. Nos. 5,175,315; 5,466,834; 5,229,526; 5,274,124;

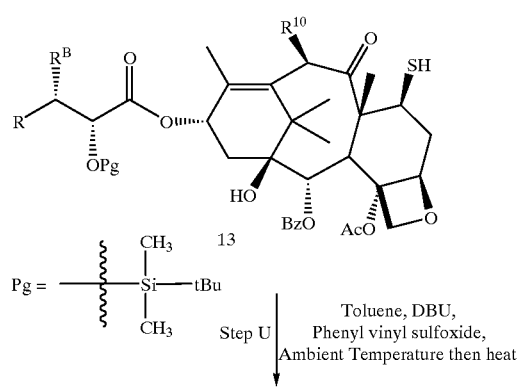

17
-continued

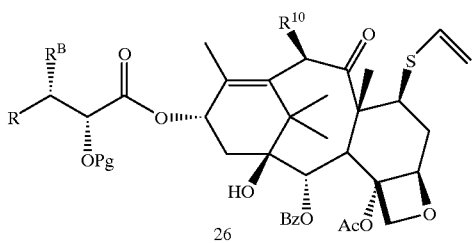

26

Step V | nBu$_4$F⁻, THF

18
-continued

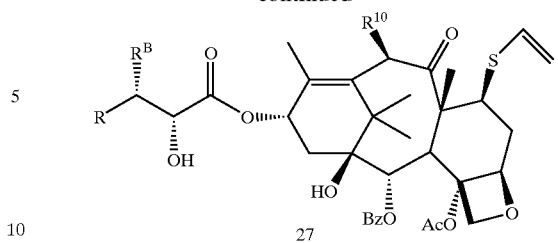

27

An alternative synthesis of substituted C-7 vinyl sulfide taxane analogs is described in Scheme XIII. The mercapto taxane 13 is allowed to add to an appropriate activated alkyne to provide directly a separable mixture of the protected E or Z substituted vinyl sulfides 32 and 33. It is preferable to separate the isomers prior to removal of the 2' protecting group but it is not essential for success of the sequence. The alkyne moiety may be substituted by any alkyl ester not just the methyl ester. In addition ketones such as methyl ethynyl ketone may be employed in the reaction. The deprotection is carried out as described in the previous schemes (e.g. Step D) to provide the desired Compounds 34 and 35.

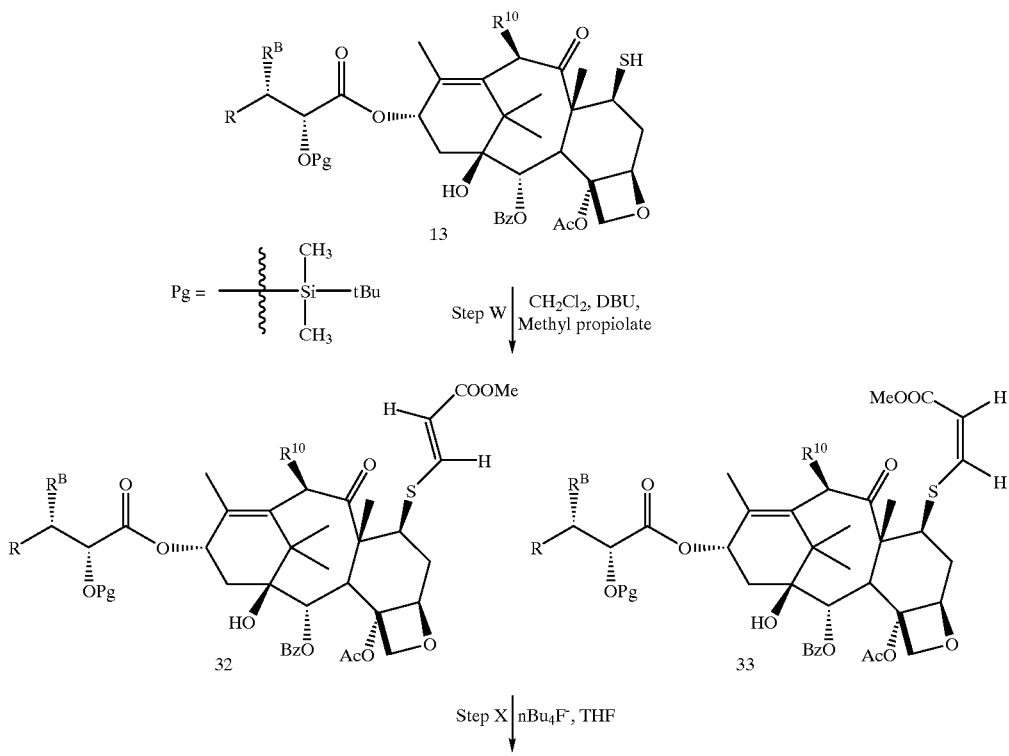

-continued

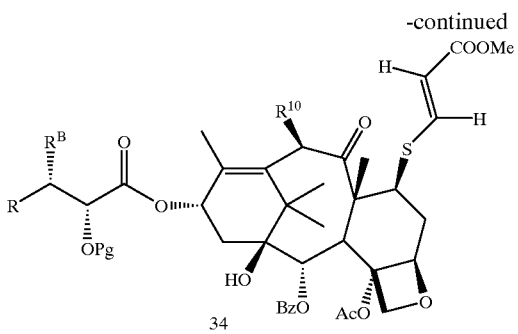

34

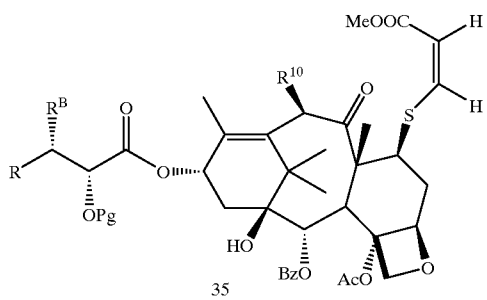

35

In addition to the methodology described above which utilizes the 7-beta triflate as the starting material for synthesis, the analogs may be prepared form 7-epihydroxy or the 7-epi mesylate starting materials using alternate chemistry and a direct displacement by sulfur nucleophiles to install the sulfur moiety in the beta orientation.

By now there are many publications teaching the introduction of a wide variety of groups onto a taxane core. By using these well established methods or obvious variants thereof, the starting taxanes of formula I or hydroxy protected analogues thereof, can be readily made. For example, for making C7 unsubstituted (deoxy) derivatives see, European Patent Application 590,267 A2 published Apr. 6, 1994 and PCT application WO 93/06093 published Apr. 1, 1993; for making C-10 epi hydroxy or acyloxy compounds see PCT application WO 96/03394; for making C-10 deoxy C-10 alkyl analogs see PCT application WO95/33740; for making 7b,8b-methano, 6a,7a-dihydroxy and 6,7-olefin groups see, R. A. Johnson, Tetrahedron Letters, Vol. 35, No 43, pp 7893–7896 (1994), U.S. Pat. No. 5,254,580 issued Oct. 19, 1993, and European Patent Application 600,517 A1 published Jun. 8, 1994; for making C7/C6 oxirane see, X. Liang and G. I. Kingston, Tetrahedron Letters, Vol. 36, No. 17, pp 2901–2904 (1995); for making C7-epi-fluoro see, G. Roth et al, Tetrahedron Letters, Vol 36, pp 1609–1612 (1995); for forming C7 esters and carbonates see, U.S. Pat. No. 5,272,171 issued Dec. 21, 1993 and S. H. Chen et al., Tetrahedron, 49, No. 14, pp 2805–282 (1993); for 9a- and 9b-hydroxy tazanes see, L. L. Klein, Tetrahedron Letters, Vol 34, No 13, pp 2047–2050 (1993), PCT application WO 94/08984 published Apr. 28, 1994, U.S. Pat. No. 5,352,806 issued Oct. 4, 1994, PCT application WO 94/20485 published Sep. 15, 1994, and G. I. Georg. et al., Tetrahedron Letters, Vol 36, No 11, pp 1783–1786 (1995). For making sidechain variations see Robert Holton U.S. Pat. Nos. 5,175, 315 and 5,229,526.

DESCRIPTION OF SPECIFIC EMBODIMENTS

The preparation of the starting materials and final products, 1a–35a shown in Table I, which correspond to the the general structures 1–35 in Schemes I–XIII are described in the examples, and in the section just prior to the examples.

TABLE I

| Compound | R | $R^B$ | $R^{10}$ | Pg |
|---|---|---|---|---|
| 1a | Ph— | PhCOHN— | AcO— | -SitBuMe$_2$ |
| 2a | Ph— | PhCOHN— | AcO— | -SitBuMe$_2$ |
| 3a | Ph— | PhCOHN— | AcO— | -SitBuMe$_2$ |
| 4a | Ph— | PhCOHN— | AcO— | -SitBuMe$_2$ |
| 5a | Ph— | PhCOHN— | AcO— | none |

TABLE I-continued

| Compound | R | $R^B$ | $R^{10}$ | Pg |
|---|---|---|---|---|
| 6a | Ph— | PhCOHN— | AcO— | -SitBuMe$_2$ |
| 7a | Ph— | PhCOHN— | AcO— | none |
| 8a | Ph— | PhCOHN— | AcO— | -SitBuMe$_2$ |
| 9a | Ph— | PhCOHN— | AcO— | none |
| 10a | Ph— | PhCOHN— | AcO— | -SitBuMe$_2$ |
| 12a | Ph— | PhCOHN— | AcO— | -SitBuMe$_2$ |
| 13a | Ph— | PhCOHN— | AcO— | -SitBuMe$_2$ |
| 14a | Ph— | PhCOHN— | AcO— | none |
| 15a | Ph— | PhCOHN— | AcO— | -SitBuMe$_2$ |
| 16a | Ph— | PhCOHN— | AcO— | none |
| 17a | Ph— | PhCOHN— | AcO— | -SitBuMe$_2$ |
| 18a | Ph— | PhCOHN— | AcO— | none |
| 19a | Ph— | PhCOHN— | AcO— | -SitBuMe$_2$ |
| 20a | Ph— | PhCOHN— | AcO— | none |
| 22a | Ph— | (CH$_3$)$_3$COCOHN— | AcO— | none |
| 24a | Ph— | PhCOHN— | AcO— | none |
| 25a | Ph— | PhCOHN— | AcO— | none |
| 27a | Ph— | PhCOHN— | AcO— | none |
| 28a | Ph— | PhCOHN— | AcO— | none |
| 29a,b | Ph— | PhCOHN— | AcO— | none |
| 30a | Ph— | PhCOHN— | AcO— | none |
| 31a,b | Ph— | PhCOHN— | AcO— | none |
| 34a | Ph— | PhCOHN— | AcO— | none |
| 35a | Ph— | PhCOHN— | AcO— | none |

The specific examples that follow illustrate the syntheses of the compounds of the instant invention, and is not to be construed as limiting the invention in sphere or scope. The method may be adapted to variations in order to produce the compound embraced by the invention but not specifically disclosed. Further, variations of the methods to produce the same compound in somewhat different manner will also be evident to one skilled in the art.

In the following experimental procedures, all temperatures are understood to be in Centigrade (C.) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet or doublet (dd), doublet of triplet (dt), and doublet of quartet (dq). The solvents employed for taking NMR spectra are acetone-d$_6$ (deuterated acetone). DMSO-d$_6$ (perdeuterodimethylsulfoxide), D$_2$O (deuterated water), CDCl$_3$ (deuterochloroform) and other conventional deuterated solvents. The infrared (IR) spectral description include only absorption wave numbers (cm$^{-1}$) having functional groups identification value.

Celite is a registered trademark of the Johns-Manville Products Corporation for diatomaceous earth.

Silica gel used in the following experimentals is silica gel 60 with a particle size 230–400 mesh obtained from EM Separations Technology.

The abbreviations used herein are conventional abbreviations widely employed in the art. Some of which are: DAB (deacetylbaccatin III); MS (mass spectrometry); HRMS (high resolution mass spectrometery); Ac (acetyl); Ph (phenyl); v/v (volume/volume); FAB (fast atom bombardment); NOBA (m-nitrobenzyl alcohol); min (minute(s)); h or hr(s) (hour(s)); DCC (1,3-dicyclohexylcarbodiimide); BOC (t-butoxycarbonyl); CBZ or Cbz (benzyloxycarbonyl); Bn (benzyl); Bz (benzoyl); Troc (2,2,2-trichloroethyoxycarbonyl), DMS (dimethylsilyl), TBAF (tetrabutylammonium fluoride), DMAP (4-dimethylaminopyridine); TES (triethylsilyl); DMSO (dimethylsulfoxide); THF (tetrahydrofuan); HMDS (hexamethyldisilazane); MeOTf (methyltriflate); NMO (morpholine-N-oxide); (DHQ)$_2$PHAL (hydroquinine 1,4-phthalazinediyl diether). Tf=triflate=trifluoromethanesulfonate; LRMS (low resolution mass spectrometry); ESI (electrospray ionization); TEMPO (2,2,6,6-tetramethyl-1-piperidinyloxy, free radical); DBU (diazobicycloundecene); MOMCl (chloromethyl methyl ether); TPAP (tetrapropyl ammonium peruthenate); MCPBA (meta chloroperoxy benzoic acid); LDA (lithium diisopropyl amide); DMF (dimethylformamide); TBS (tert-butyl-dimethylsilyl); 18-crown-6 (1,4,7,10,13,16-hexaoxacyclo-octadecane); DEAD (diethylazodicarboxylate).

Preparation of Starting Materials (Scheme I)
2'-O-(t-butyldimethylsilyl)paclitaxel [2a]

A solution of paclitaxel (1a)(17.54 gm, 20.54 mmol), imidazole (3.87 gm, 2.8 equiv) and t-butyldimethylsilyl chloride (4.96 gm, 1.6 equiv) in dry N,N-dimethylformamide (42 mL) under a dry nitrogen atmosphere was heated at 60° C. for 1.5 hour. After cooling to room temperature, the reaction mixture was partitioned between a mixture of EtOAc:hexane:=3:2 and water. The organic phase was separated and washed with water (3 times) and brine and then dried (Na$_2$SO$_4$). Removal of the solvents followed by silica gel column chromatography (elution with 500 mL portions of hexane containing 100, 150, 200, 250, 300 mL of EtOAc) afforded 19.7 gm (99% yield) 2'-O-(t-butyldimethylsilyl)paclitaxel.

2'-O-(t-Butyldimethylsilyl)-7β-O-trifluormethanesulfonylpaclitaxel [3a]

A solution of 2'-O-(t-butyldimethylsilyl)paclitaxel (2a) (19.7 gm, 20.3 mmole) and 4-dimethylaminopyridine (4.96 gm, 40.6 mmol) in dry CH$_2$Cl$_2$ (40 mL) under an atmosphere of dry nitrogen was cooled in an ice bath. Trifluoromethanesulfonic anhydride (3.76 mL, 22.3 mmol) was slowly added with stirring and a white precipitate formed. The reaction was removed from the bath after 20 min and was left stirring at room temperature for 45 min. It was then partitioned between water and a mixture of EtOAc:hexane=3:2. The organic phase as removed and washed with water (3 times), brine and dried (Na$_2$SO$_4$). Removal of the solvent followed by silica gel column chromatography (elution with 500 mL portions of hexane containing 100, 125, 150, 175 (twice) mL of EtOAc) afforded 21.9 gm (98% yield) of 2'-O-(t-butyldimethylsilyl)-7-O-trifluoromethanesulfonylpaclitaxel: $^1$H NMR (CDCl$_3$) δ-0.32 (s, 3H), -0.04 (s, 3H), 0.77 (s, 9H), 1.16 (s, 3H), 1.20 (s, 3H), 1.87 (s, 3H), 2.05 (s, 3H), 2.17 (s, 3H), 2.58 (s, 3H), 2.0–2.4 (m, 3H), 2.85 (m, 1H), 3.95 (d, 1H, J=6.9 Hz), 4.20 (d, 1H, J=8.5 Hz), 4.35 (d, 1H, J=8.5 Hz), 4.64 (d, 1H, J=2.1 )Hz), 4.92 (d, 1H, J=8.7 Hz), 5.47 (dd, 1H, J=7.5, 10.2 Hz), 5.73 (m, 2H), 6.24 (m, 1H), 6.60 (s, 1H), 7.04 (d, 1H, J=9.0 Hz) 7.3–8.1 (m, 15H).

EXAMPLE 1

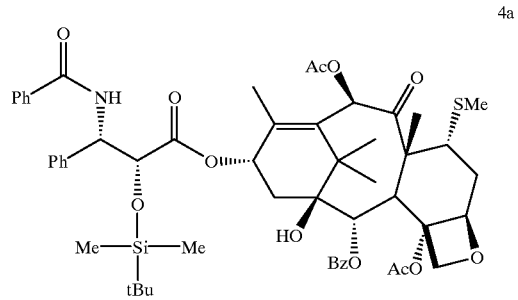

A solution of 2'-O-(t-butyldimethylsilyl)-7β-O-trifluoromethanesulfonyl-paclitaxel (3a) (240 mg, 0.237 mmole) in 2 mL of dry dimethylformamide was cooled in an acetone/ice bath at about −10° C. under a dry nitrogen atmosphere. Powdered lithium thiomethoxide (Prepared by the method of T. R. Kelly et al., Tetrahedron Letters, 1977, 3859) (30 mg, 2.5 equiv) were added and the reaction was then left stirring for 2 hr while maintaining the bath temperature below 0° C. The reaction was then quenched by adding a saturated solution of NH$_4$Cl with vigorous stirring. After partitioning the resulting mixture between EtOAc and water, the organic phase was separated and washed with water (3 times) brine and dried (Na$_2$SO$_4$). Removal of the solvents was followed by chromatography on a silica gel preparative tlc plate (2 mm, developed 3 times with a mixture of EtOAc:hexane=1:3) to afford 82 mg (38%) of 2'-O-(t-butyldimethylsilyl)-7-deoxy-7α-thiomethylpaclitaxel (4a):

$^1$H NMR (CDCl$_3$) δ-0.36 (s, 3H), -0.07 (s, 3H), 0.76 (s, 9H), 1.18 (s, 3H), 1.16 (s, 3H), 1.62 (s, 3H), 1.81 (s, 3H), 2.02 (s, 3H), 2.2–2.7 (m, 5H), 2.10 (s, 3H), 2.58 (s, 3H), 4.01 (d, 1H, J=7.0 Hz), 4.32 (d, 1H, J=8.3 Hz) 4.62 (d, 1H, J=8.3 Hz), 4.66 (d, 1H, J=1.7 Hz), 5.00 (m, 1H), 5.70 (d, 1H, J=7.0 Hz), 5.78 (d, 1H, J=9.7 Hz), 6.27 (m, 1H), 7.08 (d, 1H, J=9.0 Hz), 7.26–7.61 (m, 12H), 7.74 (d, 2H, J=7.3 Hz), 8.13 (d, 2H, J=7.0 Hz); LRMS (ESI) 998 ([M+H]$^+$).

EXAMPLE 2

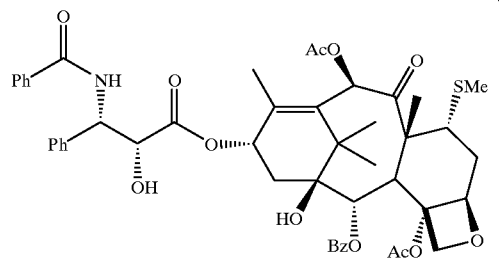

A solution of 2'-O-(t-butyldimethylsilyl)-7-deoxy-7α-thiomethylpaclitaxel (4a) (195 mg, 0.195 mmole) in dry THF (2 mL) and under a dry nitrogen atmosphere was cooled in an acetone/ice bath at about −10° C. A solution of tetrabutylammonium fluoride (0.22 mL, 1.0 M in THF, 1.1 equiv) was added. After 20 min, the reaction was quenched by adding a saturated solution of NH₄Cl with vigourous stirring. This was extracted with EtOAc (3 times) and the combined organic extracts were washed with brine and dried (Na₂SO₄). Removal of the solvents was followed by chromatography on a silica gel preparative tlc plate (2 mm, developed 3 times with a mixture of EtOAc:hexane=3:2) to afford 140 mg (81%) of 7-deoxy-7α-thiomethylpaclitaxel (5a):

¹H NMR (CDCl₃) δ1.16 (s, 3H), 1.17 (s, 3H), 1.80 (s, 3H), 1.88 (s, 3H), 2.09 (s, 3H), 2.18 (s, 3H) 2.3–2.6 (m, 5H), 2.41 (s, 3H), 3.42 (d, 1H, J=4.6 Hz), 4.00 (d, 1H, J=7.0 Hz), 4.28 (d, 1H, J=8.2 Hz), 4.61 (d, 1H, J=4.6 Hz), 4.79 (dd 1H, J=2.4, 4.6 Hz), 4.95 (m, 1H), 5.69 (d, 1H, J=7.0 Hz), 5.84 (dd, 1H, J=1.9, 9.5 Hz), 5.82 (m, 1H), 7.01 (d, 1H, J=9.2 Hz), 7.19 (s, 1H), 7.32–7.62 (m, 11H), 7.74 (d, 2H, J=7.7 Hz), 8.13 (d, 2H, J=7.7 Hz); LRMS (negative ESI) 882 ([M−H]⁻).

EXAMPLE 3

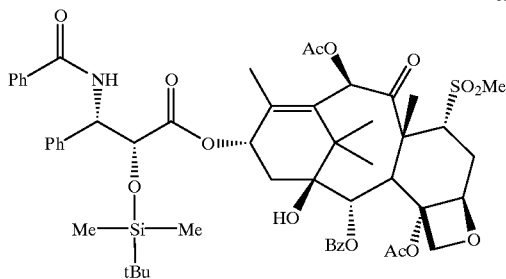

6a

A solution of 2'-O-(t-butyldimethylsilyl)-7-deoxy-7α-thiomethylpaclitaxel (4a) (446 mg, 0.447 mmole) in CH₂Cl₂ (4 mL) was cooled in an ice bath and solid m-chloroperbenzoic acid (0.238 gm, 80%, 2.5 equiv) was added. The reaction was removed from the bath and left stirring at rt for 1.5 hr. It was then diluted with EtOAc and washed with: 10% aqueous solution of NaHSO₃; saturated aqueous NaHCO₃ solution (4 times); brine; and then dried (Na₂SO₄). Removal of the solvents followed by chromatography on two silica gel preparative tlc plates (2 mm, developed 3 times with a mixture of EtOAc:hexane=30:70) to afford 288 mg (63%) of 2'-O-(t-butyldimethylsilyl)-7-deoxy-7α-methylsulfonylpaclitaxel (6a):

¹H NMR (CDCl₃) δ-0.36 (s, 3H), -0.07 (s, 3H), 0.76 (s, 9H), 1.18 (s, 3H), 1.22 (s, 3H), 1.96 (s, 3H), 2.01 (s, 3H), 2.17 (s, 3H), 2.1–2.8 (m, 4H), 2.95 (s, 3H), 3.65 (m, 3H), 4.13 (d, 1H, J=6.8 Hz), 4.52 (d, 1H, J=8.6 Hz) 4.57 (d, 1H, J=8.6 Hz), 4.64 (d, 1H, J=1.7 Hz), 5.36 (m, 1H), 5.77 (m, 2H), 6.28 (m, 1H), 7.08 (d, 1H, J=9.1 Hz), 7.23 (s, 1H), 7.3–7.6 (m, 12H), 7.74 (d, 2H, J=7.1 Hz), 8.08 (d, 2H, J=7.1 Hz); LRMS (negative ESI) 1028 ([M−H]⁻); IR (KBr disk) 1315 cm⁻¹.

EXAMPLE 4

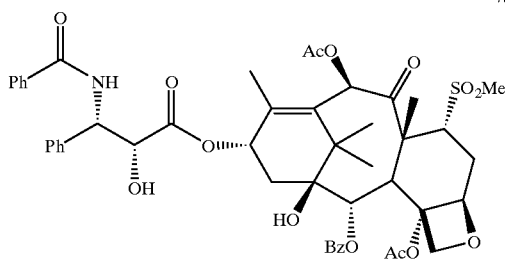

7a

A solution of 2'-O-(t-butyldimethylsilyl)-7-deoxy-7α-methylsulfonylpaclitaxel (6a) (130 mg, 0.126 mmole) in dry THF (1 mL) and under a dry nitrogen atmosphere was cooled in an acetone/ice bath at about −10° C. A solution of tetrabutylammonium fluoride (0.14 mL, 1.0 M in THF, 1.1 equiv) was added. After 20 min, the reaction was quenched by adding a saturated solution of NH₄Cl with vigourous stirring. This was extracted with EtOAc (3 times) and the combined organic extracts were washed with brine and dried (Na₂SO₄). Removal of the solvents was followed by chromatography on a silica gel preparative tlc plate (2 mm, developed 2 times with a mixture of EtOAc:hexane=3:1) to afford 77 mg (67%) of 7-deoxy-7α-methylsulfonylpaclitaxel (7a):

¹H NMR (CDCl₃) δ1.17 (s, 3H), 1.22 (s, 3H), 1.88 (s, 3H), 1.92 (s, 3H), 2.17 (s, 3H), 2.40 (s, 3H), 2.2–2.7 (m, 4H), 2.94 (s, 3H), 3.63 (m, 1H), 4.14 (d, 1H, J=6.4 Hz), 4.5 (br s, 1H), 4.54 (d, 1H,J=8.5 Hz), 4.46 (d, 1H,J=8.5 Hz), 4.78 (d, 1H, J=1.8 Hz), 5.29 (m, 1H), 5.78 (d, 1H, J=6.4 Hz), 5.84 (dd, 1H, J=1.8, 9.2 Hz), 6.20 (m, 1H), 7.04 (d, 1H, J=9.2 Hz), 7.16 (s, 1H), 7.2–7.6 (m, 11H), 7.74 (d, 2H, J=7.8 Hz), 8.09 (d, 2H, J=7.8 Hz); LRMS (negative ESI) 914 ([M−H]⁻); IR (KBr disk) 1315 cm⁻¹.

EXAMPLE 5

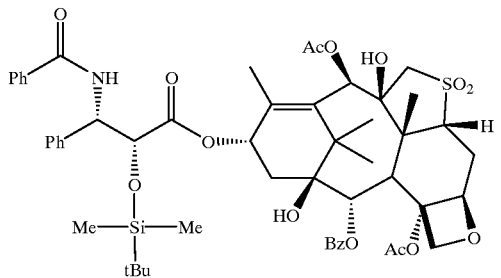

8a

A solution of 2'-O-(t-butyldimethylsilyl)-7-deoxy-7α-methylsulfonylpaclitaxel (6a) (155 mg, 0.151 mmole) in dry THF (1.5 mL) under a nitrogen atmosphere was cooled to −78° C. and a solution of LiHMDSA (0.30 mL, 1.0 M in THF 2 equiv) was added dropwise. A thick gel forms within 10 min and the reaction was removed from the bath. After 15 min the gel had turned into a liquid and a saturated solution of NH₄Cl was added with vigorous stirring. This mixture was extracted with EtOAc and the extract was washed with brine and dried (Na₂SO₄). Removal of the solvents was followed by chromatography on a silica gel preparative tlc plate (2 mm, developed 2 times with a mixture of EtOAc:hexane=1:1) to afford 91 mg (61%) of the desired product (8a):

$^1$H NMR (CDCl$_3$) δ -0.39 (s, 3H), -0.02 (s, 3H), 0.76 (s, 9H), 1.24 (s, 3H), 1.70 (s, 3H), 1.83 (s, 3H), 1.97 ((s, 3H), 2.12 (s, 3H), 2.1–2.5 (m, 3H), 2.54 (s, 3H), 2.68 (t, 1H, J=13.6 Hz), 3.16 (d, 1H,J=14.0 Hz), 3.37 (s, 1H), 3.40 (d, 1H, J=14.2 Hz), 3.57 (d, 1H, J=3.6 Hz), 3.77 (dd, 1H, J=6.2, 13.4 Hz), 4.20 (d, 1H, J=7.9 Hz), 4.51 (d, 1H, J=7.9 Hz), 4.69 (d, 1H, J=1.7 Hz), 5.32 (d, 1H, J=3.5 Hz), 5.77 (d, 1H, J=9.0 Hz), 6.10 (d, 1H, J=3.8 Hz), 6.28 (m, 1H), 6.77 (s, 1H), 7.09 (d, 1H, J=9.0 Hz), 7.3–7.8 (m, 11H), 7.76 (m, 2H), 8.07 (m, 2H).

EXAMPLE 6

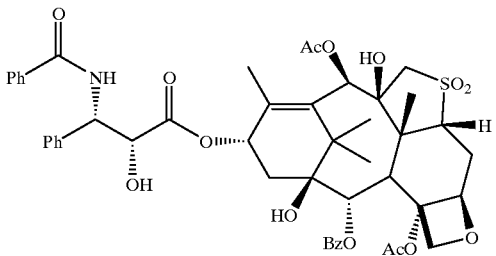

9a

A solution of the 2'-O-(t-butyldimethylsilyl)-derivative (8a) (94 mg, 0.91 mmole) in dry THF (1 mL) and under a dry nitrogen atmosphere was cooled in an acetone/ice bath at both −10° C. A solution of tetrabutylammonium fluoride (0.10 mL, 1.0 M in THF, 1.1 equiv) was added. After 5 min, the reaction was quenched by adding a saturated solution of NH$_4$Cl with vigourous stirring. This was extracted with EtOAc (3 times) and the combined organic extracts were washed with brine and dried (Na$_2$SO$_4$). Removal of the solvents was followed by chromatography on a silica gel preparative tlc plate (2 mm, developed with a mixture of EtOAc:hexane=65:35) to afford 63 mg (76%) of the desired product (9a):

$^1$H NMR (CDCl$_3$) δ 1.09 (s, 3H), 1.59 (s, 3H), 1.69(s, 3H), 1.72 (s, 3H), 2.01 (s, 3H), 2.21 (s, 3H), 2.0–2.4 (m, 3H), 2.54 (m, 1H), 3.07 (d, 1H, J=14.1 Hz), 3.31 (d, 1H, J=14.1 Hz), 3.40 (s, 1H), 3.48 (d, 1H, J=3.5 Hz), 3.65 (dd, 1H, J=6.2, 13.2 Hz), 4.11 (d, 1H, J=8.0 Hz), 4.41 (d, 1H, J=8.0 Hz), 4.63 (m, 1H), 4.73 (s, 1H), 5.14 (d, 1H,J=3.5 Hz), 5.78 (d, 1H, J=7.8 Hz), 6.06 (m, 1H), 6.57 (s, 1H), 7.3–7.8 (m, 12H), 7.81 (m, 2H),8.05 (m, 2H); LRMS (ESI) 916 ([M+H]$^+$).

EXAMPLE 7

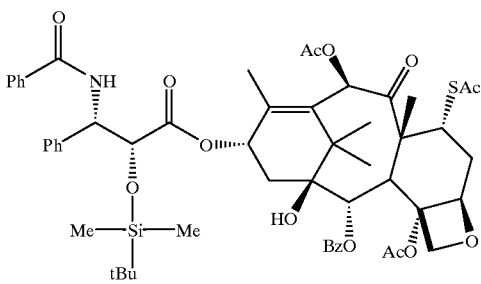

10a

Potassium thioacetate (7.30 gm, 10 equiv) was added to a stirred solution of 2'-O-(t-butyldimethylsilyl)-7β-O-trifluoromethanesulfonylpaclitaxel (3a) (7.07 g, 6.40 mmole) in 64 mL of absolute EtOH at room temperature under a dry nitrogen atmosphere. After stirring for 45 hr in the dark, the reaction was partitioned between a mixture of EtOAc:hexane=1:1 and water, the organic phase was separated and washed with water (2 times), brine and dried (Na$_2$SO$_4$). Removal of the solvents was followed by chromatography on a silica gel column (gradient elution with mixtures of EtOAc:hexane=1:4 to 7:13) to afford 5.82 gm (89%) of 2'-O-(t-butyldimethylsilyl)-7-deoxy-7α-thioacetoxy paclitaxel (10a): $^1$H NMR (CDCl$_3$) δ -0.33 (s, 3H), -0.05 (s, 3H), 0.78 (s, 9H), 1.12 (s, 3H), 1.17 (s, 3H), 1.8–2.4 (m, 4H), 2.04 (s, 3H), 2.13 (s, 3H), 2.43 (s, 3H), 2.63 (s, 3H), 3.89 (d, 1H, J=7.0 Hz), 4.00 (m, 1H), 4.28 (d, 1H, J=8.3 Hz), 4.64 (d, 1H, J=8.4 Hz), 4.68 (d, 1H, J=1.9 Hz), 4.85 (m, 1H), 5.69 (d, 1H, J=7.0 Hz), 5.80 (br d, 1H, J=8.5 Hz), 6.29 (m, 1H), 6.89 (s, 1H), 7.06 (d, 1H, J=9.0 Hz), 7.3–7.6 (m, 11H), 7.74 (m, 2H), 8.15 (m, 2H); LRMS (ESI) 1026 ([M+H]$^+$).

EXAMPLE 8

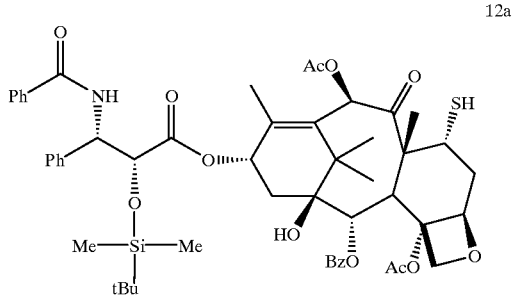

12a

A solution of 2'-O-(t-butyldimethylsilyl)-7-deoxy-7α-thioacetoxy paclitaxel (10a) (0.96 gm, 0.94 mmole) in anhydrous EtOH (50 mL) was sparged with dry nitrogen for 45 min. This solution was then saturated with anhydrous NH$_3$ and then left stirring at room temperature for 1 hr. It was sparged with dry nitrogen for 20 min and the solvent was removed. The residue was chromatographed on a silica gel column (elution with 200 mL portions of hexane containing 50, 60, 70, 80 (twice) mL of EtOAc) to afford 0.57 gm (61%) of slightly impure 2'-O-(t-butyldimethylsilyl)-7-deoxy-7α-thiopaclitaxel (12a): $^1$H NMR (CDCl$_3$) δ -0.34 (s, 3H), -0.07 (s, 3H), 0.76 (s, 9H), 1.15 (s, 3H), 1.18 (s, 3H), 1.84 (s, 3H), 1.97 (s, 3H), 2.1–2.6 (m, 4H), 2.17 (s, 3H), 2.63 (s, 3H), 2.93 (m, 1H), 3.70 (d, 1H, J=13.0 Hz), 4.06 (d, 1H, J=7.1 Hz), 4.26 (d, 1H, J=8.4 Hz), 4.67 (m, 2H), 4.95 (m, 1H, 5.71 (d, 1H, J=6.8 Hz), 5.78 (d, 1H, J=8.9 Hz), 6.28 (m, 1H), 7.07 (d, 1H, J=8.9 Hz), 7.2–7.6 (m, 12Hz), 7.74 (d, 2H, J=7.4 Hz), 8.15 (d, 2H, J=7.9 Hz); LRMS (ESI) 984 ([M+H]$^+$).

EXAMPLE 9

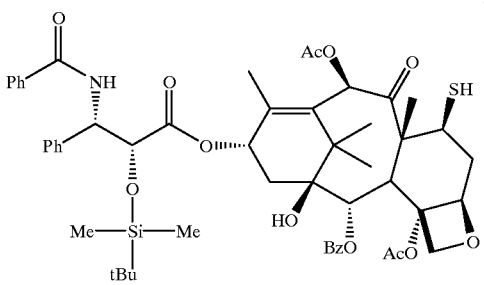
13a

A solution of 2'-O-(t-butyldimethylsilyl)-7-deoxy-7α-thiopaclitaxel (12a) (500 mg, 0.508 mmole) in dry toluene (20 mL) at room temperature was sparged with dry nitrogen for 20 min. 1.8-Diazabicyclo[5.4.0]undec-7-ene (0.152 mL, 2 equiv) was added and the reaction was placed in an oil bath at approximately 95° C. The isomerization of the starting material into its 7β-isomer was monitored by HPLC (Vydac 218TP reverse phase column, gradient elution: 75% aqueous $CH_3CN$ to 100% $CH_3CN$ over 9 min at 2 mL per min). After 18.5 hr, the ratio of 7α to 7β-thiol isomers was about 1:9 and the reaction was allowed to cool to room temperature and diluted with a mixture of EtOAc:hexane=3:2. This was washed with saturated aqueous $NH_4Cl$ (twice), brine, and then dried ($Na_2SO_4$). Removal of the solvents followed by radial chromatography (1 mm silica gel plate, gradient elution with mixtures of EtOAc:hexane=1:4 to 7:13) afforded 344 mg (69%) of 2'-O-(t-butyldimethylsilyl)-7-deoxy-7α-thiopaclitaxel (13a): $^1H$ NMR ($CDCl_3$) δ-0.31 (s, 3H), 0.79 (s, 9H), 1.17 (s, 3H), 1.20 (s, 3H), 1.69 (s, 3H), 1.8–2.2 (m, 3H), 1.91 (s, 3H), 2.40 (dd, 1H, J=9.3, 15.3 Hz), 2.21 (s, 3H), 2.56 (s, 3H), 2.68 (m, 1H), 3.84 (d, 1H, J=6.7 Hz), 4.17 (d, 1H, J=8.4 Hz), 4.32 (d, 1H, J=8.4 Hz), 4.65 (d, 1H, J=2.1 Hz), 4.94 (d, 1H, J=9.3 Hz), 5.69 (m, 2H), 6.23 (m, 1H), 6.28 (s, 1H), 7.05 (d, 1H, J=8.8 Hz), 7.3–7.6 (m, 11H), 7.73 (d, 2H, J=7.2 Hz), 8.11 (d, 2H, J=7.2 Hz); LRMS (ESI) 984 ([M+H]$^+$).

EXAMPLE 10

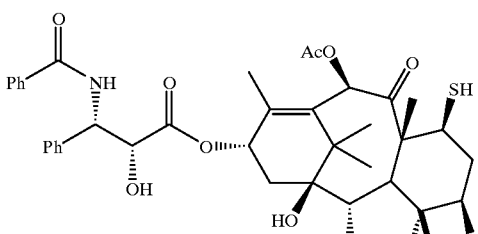
14a

A solution of 2'-O-(t-butyldimethylsilyl)-7-deoxy-7β-thiopaclitaxel (13a) (234 mg, 0.238 mmole) in dry THF (3 mL) and under a dry nitrogen atmosphere was cooled in an ice bath. A solution of tetrabutylammonium fluoride (0.26 mL, 1.0 M in THF, 1.1 equiv) was added. After 5 min, the reaction was quenched by adding a saturated solution of $NH_4Cl$ with vigourous stirring. This was extracted with EtOAc (2 times) and the combined organic extracts were washed with brine and dried ($Na_2SO_4$). Removal of the solvents was followed by column chromatography on silica gel (elution with 100 mL portions of hexane containing 30, 35, 40, 45, 50, 55 mL of EtOAc) to afford 115 mg (56%) of 7-deoxy-7β-thiomethylpaclitaxel (14a): $^1H$ NMR ($CDCl_3$) δ1.19 (s, 3H), 1.18 (s, 3H), 1.69 (s, 3H), 1.76 (s, 3H), 1.8–2.3 (m, 4H), 2.221 (s, 3H), 2.36 (s, 3H), 2.66 (m, 1H), 3.53 (m, 1H), 3.61 (br s, 1H), 3.79 (d, 1H, J=6.6 Hz), 4.15 (d, 1H, J=8.4 Hz), 4.29 (d, 1H, J=8.4 Hz), 4.77 (br s, 1H), 4.90 (d, 1H, J=8.8 Hz), 5.67 (d, 1H, J=6.6 Hz), 5.78 (br d, 1H, J=8.1 Hz), 6.16 (m, 1H), 6.24 (s, 1H), 7.02 (d, 1H, J=8.8 Hz), 7.2–7.6 (m, 11H), 7.74 (d, 2H, J=8.0 Hz), 8.09 (d, 2H, J=8.0 Hz); LRMS (negative ESI) 868 ([M–H]$^-$).

EXAMPLE 11

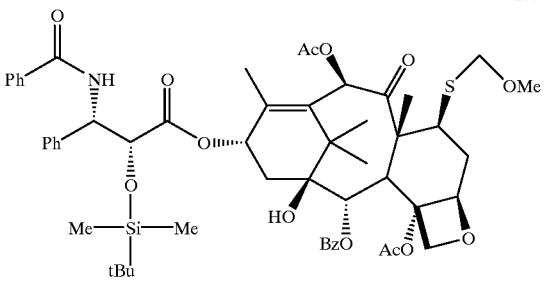
15a

Bromomethyl methyl ether (0.006 mL, 1.1 equiv) was added to a solution of 2'-O-(t-butyldimethylsilyl)-7-deoxy-7β-thiopaclitaxel (13a) (61 mg, 0.062 mmole) and 1,8-diazabicyclo[5.4.0]undec-7-ene (0.152 mL, 1.5 equiv) in dry $CH_2Cl_2$ (1 mL) and under a dry nitrogen atmosphere. After 10 min, the reaction was diluted with a mixture of EtOAc:hexane=3:2. It was then washed with saturated aqueous $NH_4Cl$ (twice), brine, and dried ($Na_2SO_4$). Removal of the solvents was followed by radial chromatography (1 mm silica gel plate, gradient elution with mixtures of EtOAc:hexane=1:4 to 7:13) to afford 43 mg (67%) of 2'-O-(t-butyldimethylsilyl)-7-deoxy-7β-thiomethoxymethylpaclitaxel (15a): $^1H$ NMR ($CDCl_3$) δ-0.32 (s, 3H), -0.04 (s, 3H), 0.78 (s, 9H), 1.17 (s, 3H), 1.22 (s, 3H), 1.73 (s, 3H), 2.0–2.4 (m, 3H), 2.01 (s, 3H), 2.18 (s, 3H), 2.56 (s, 3H), 2.84 (m, 1H), 3.34 (s, 3H), 3.37 (m, 1H), 3.89 (d, 1H, J=6.7 Hz), 4.18 (d, 1H, J=8.5 Hz), 4.34 (d, 1H, J=8.5 Hz), 4.62 (d, 1H, J=11.9 Hz), 4.65 (d, 1H, J=1.8 Hz), 4.70 (d, 1H, J=11.9 Hz), 4.96 (d, 1H, J=8.3 Hz), 5.66 (d, 1H, J=6.7 Hz), 5.72 (d, 1H, J=8.9 Hz), 6.24 (m, 1H), 6.49 (s, 1H), 7.06 (d, 1H, J=8.9 Hz), 7.3–7.6 (m, 11H), 7.73 (d, 2H, J=7.9 Hz), 8.11 (d, 2H, J=7.9 Hz); LRMS (ESI) 1028 ([M+H]$^+$).

EXAMPLE 12

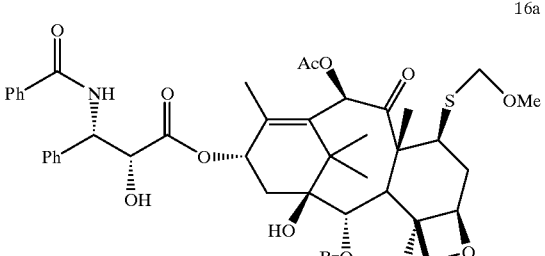
16a

A solution of tetrabutylammonium fluoride (0.57 mL, 1.0 M in THF, 1.1 equiv) was added to a solution of (15a)

2'-O-(t-butyldimethylsilyl)-7-deoxy-7β-thiomethoxymethyl paclitaxel (511 mg, 0.516 mmole) in dry THF (5 mL) that was in an ice bath and maintained under a dry nitrogen atmosphere. After 5 min, the reaction was quenched by adding a saturated solution of NH$_4$Cl with vigourous stirring. This was extracted with EtOAc (3 times) and the combined organic extracts were washed with brine and dried (Na$_2$SO$_4$). Removal of the solvents was followed by column chromatography on silica gel (elution with 100 mL portions of hexane containing 30, 35, 40, 45, 50, 55 60 mL of EtOAc) to afford 365 (77%) of 7-deoxy-7β-thiomethoxymethyl paclitaxel (16a): $^1$H NMR (CDCl$_3$) δ1.16 (s, 3H), 1.22 (s, 3H), 1.56 (s, 3H), 1.85 (s, 3H), 2.18 (s, 3H), 2.0–2.4 (m, 3H), 2.35 (s, 3H), 2.82 (m, 1H), 3.31 (m, 1H), 3.32 (s, 1H), 3.66 (d, 1H, J=4.6 Hz), 3.82 (d, 1H, J=6.5 Hz), 4.15 (d, 1H, J=8.3 Hz), 4.30 (d, 1H, J=8.3 Hz), 4.58 (d, 1H, J=11.9 Hz), 4.70 (d, 1H, J=11.9 Hz), 4.77 (dd, 1H, J=2.6, 4.6 Hz), 4.92 (d, 1H, J=9.3 Hz), 5.62 (d, 1H, J=6.7 Hz), 5.79 (m, 1H), 6.15 (m, 1H), 6.46 (s, 1H), 7.07 (d, 1H, J=8.9 Hz), 7.3–7.6 (m, 11H), 7.76 (m, 2H), 8.08 (d, 2H); LRMS (ESI) 914 ([M+H]$^+$).

EXAMPLE 13

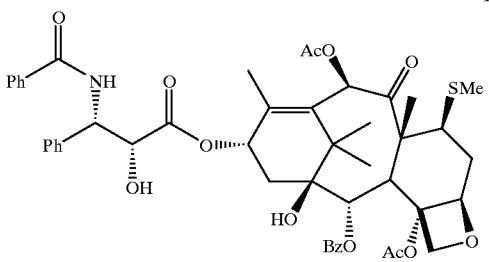

18a

Iodomethane (0.100 mL, 1.1 equiv) was added to a solution of 7-deoxy-7β-thiopaclitaxel (14a) (1.30 gm, 1.49 mmole) and 1,8-diazabicyclo[5.4.0]undec-7-ene (0.33 mL, 1.5 equiv) in dry CH$_2$Cl$_2$ (14 mL) and under a dry nitrogen atmosphere. After 5 min, the reaction was diluted with CH$_2$Cl$_2$, washed with saturated aqueous NH$_4$Cl, water, and dried (Na$_2$SO$_4$). Removal of the solvents was followed by radial chromatography (2 mm silica gel plate, gradient elution with mixtures of EtOAc:hexane=1:4 to 1:3) to afford 1.04 gm (79%) of 7-deoxy-7β-thiomethylpaclitaxel (18a): $^1$H NMR (CDCl$_3$) δ1.16 (s, 3H), 1.21 (s, 3H), 1.70 (s, 3H), 1.84 (s, 3H), 2.09–2.27 (m, 3H), 2.12 (s, 3H), 2.19 (s, 1H), 2.35 (s, 3H), 2.73 (m, 1H)m, 3.04 (dd, 1H, J=6.5, 11.8 Hz), 3.67 (m, 1H), 3.80 (d, 1H, J=6.6 Hz), 4.14 (d, 1H, J=8.4 Hz), 4.30 (d, 1H, J=8.4 Hz), 4.77 (br s, 1H), 4.94 (d, 1H, J=8.1 Hz), 5.61 (d, 1H, J=6.6 %Hz), 5.78 (dd, 1H, J=2.4, 8.9 Hz), 6.14 (m, 1H), 6.53 (s, 1H), 7.07 (d, 1H, J=8.9 Hz), 7.3–7.6 (m, 11H), 7.75 (d, 2H, J=7.2 Hz), 8.08 (d, 2H, J=7.2 Hz); LRMS (negative ESI) 882 ([M–H]$^-$).

EXAMPLE 14

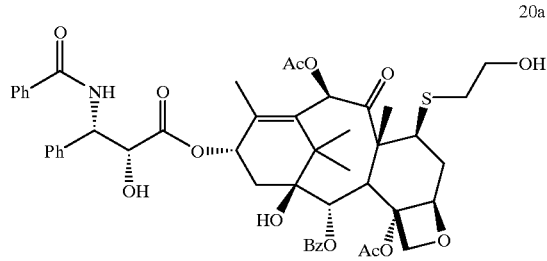

20a 1,8-Diazabicyclo[5.4.0]undec-7-ene (0.015 mL, 0.1 equiv) was added to a solution of 2'-O-(t-butyldimethylsilyl)-7-deoxy-7β-thiopaclitaxel (13a) (984 mg, 1.0 mmole) in dry benzene (25 mL) that had been saturated with ethylene oxide. After 5 hr, the solvent was removed and the residue was chromatographed (silica gel column; eluting with a mixture of EtOAc:hexane=1:1) to afford 1.09 gm (99%) of O-(t-butyldimethylsilyl)-7-deoxy-7β-(hydroxyethylthio)-paclitaxel (19a). This was taken, dissolved in dry THF (10 mL), and cooled in an acetone/ice bath. Tetrabutylammonium fluoride (1.1 mL, 1.0 M in THF, 1.0 equiv) was added and after 5 min, the reaction was diluted with EtOAc and a solution of KHSO$_4$ (2 mL, 1.0 M) and water were added with stirring. The organic phase was separated, washed with brine, and dried (Na$_2$SO$_4$). Removal of the solvents was followed by silica gel column chromatography (eluting with a mixtures of EtOAc:hexane:CH$_2$Cl$_2$=2:1:0.5) gave 610 mg (64%) of 7-deoxy-7β-(2-hydroxethylthio)paclitaxel (20a): $^1$H NMR (CDCl$_3$) δ1.16 (br s, 9H), 1.74 (s, 3H), 1.83 (s, 3H), 1.85 (s, 3H), 2.15–2.4 (m, 3H), 2.23 (s, 3H), 2.36 (s, 3H), 2.64–2.82 (m, 3H), 3.26 (dd, 1H, J=6.4, 11.6 Hz), 3.71 (m, 3H), 3.81 (d, 1H, J=6.7 Hz), 4.17 (d, 1H, J=8.4 Hz), 4.31 (d, 1H, J=8.4 Hz), 4.78 (br s, 1H), 4.91 (d, 1H, J=7.9 Hz), 5.63 (d, 1H, J=6.7 Hz), 5.77 (dd, 1H, J=2.3, 8.9 Hz), 6.16 (m, 1H), 6.52 (s, 1H), 7.08 (d, 1H, J=8.9 Hz), 7.51–8.09 (m, 15H); LRMS (ESI) 9.14 ([M+H]$^+$).

EXAMPLE 15

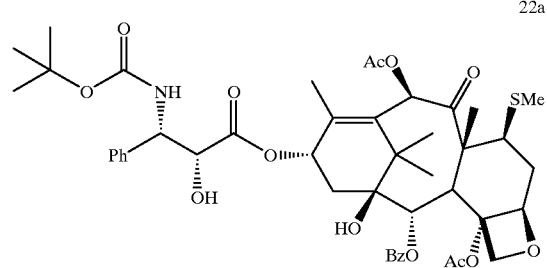

22a

Tetrabutyl ammonium borohydride (682 mg, 2 equiv.) was added to a solution of 2'-O-(t-butyldimethylsilyl)-7-deoxy-7β-thiomethylpaclitaxel (18a) (1.17 gm, 1.32 mmole) in a mixture of dry CH$_2$Cl$_2$ (12 mL) and MeOH (2.6 mL) under a nitrogen atmosphere at RT. After 7 hr, the reaction was quenched with saturated NH$_4$Cl solution and dried (Na$_2$SO$_4$). Removal of the solvents followed by radial chromatography (2 mm silica gel plate eluted with mixtures of EtOAc:hexane=7:13 to 3:2) afforded 754 mg (93%) of 7-deoxy-7β-thiomethylbaccatin (21a): $^1$H NMR (CDCl$_3$+ D$_2$O) δ1.04 (s, 3H), 1.19 (s, 3H), 1.69 (s, 3H), 2.02–2.24 (m, 3H), 2.14 (s, 3H), 2.15 (s, 3H), 2.20 (m, 3H), 2.28 (s, 3H), 2.76 (m, 1H), 3.13(dd, 1H, J=8.5, 14.1 Hz), 3.90 (d, 1H, J=6.7 Hz), 4.11 (d, 1H, J=8.3 Hz), 4.31 (d, 1H, J=8.3 Hz), 4.84 (m, 1H), 4.99 (d, 1H, J=9.3 Hz), 5.57 (d, 1H,J=6.7 Hz), 6.58 (s, 1H), 7.4–7.6 (m, 3H), 8.08 (d, 2H, J=8.1 Hz); LRMS (negative ESI) 615 ([M–H]$^-$). A solution of 7-deoxy-7β-thiomethylbaccatin (21a) (482 mg, 0.782 mmole) in dry THF (15 mL) under dry N$_2$ was cooled to −50° C. and a solution of lithium hexamethyldisilazide (1.0 M in THF, 0.94 mL, 1.2 equiv) was added. After 15 min, a solution of (3R, 4S)-1-(t-butyoxycarbonyl)-4-phenyl-3-triethylsilyloxy-2-azetidinone (649 mg, 2.2 equiv) in dry THF (15 mL) was added by cannula and the reaction was transferred to and ice bath. After 45 min, this was quenched with a saturated NH$_4$Cl solution and extracted with mixture of EtOAc:hexane=3:2. The organic extract was washed with brine and dried (Na$_2$SO$_4$). Removal of the solvents followed by radial chromatography (2 mm silica gel plate eluted with mixtures of EtOAc:hexane=1:4 to 7:13) afforded 740 mg (95%) of 2'-O-(triethylsilyl)-3'-NH-Boc-7-deoxy-7β-thiomethylpaclitaxel (22a): $^1$H NMR (CDCl$_3$) δ0.37 (m, 6H), 0.77 (t, 9H), 1.23 (s, 6H), 1.32 (s, 9H), 1.71 (s, 3H), 2.00 (s, 3H), 2.07–2.39 (m, 3H), 2.14 (s, 3H), 2.52 (s, 3H), 2.76 (m, 1H), 3.12(dd, 1H, J=6.3, 12.1 Hz), 3.88 (d, 1H, J=6.8 Hz), 4.16 (d, 1H, J=8.4 Hz), 4.33 (d, 1H, J=8.4 Hz), 4.99 (d, 1H, J=7.7 Hz), 5.27 (br d, 1H, J=8.9 Hz), 5.47 (br d, 1H, J=9.6 Hz), 5.65 (d, 1H, J=6.8 Hz), 6.23 (m, 1H), 6.59 (s, 1H),7.25–7.61 (m, 8H), 8.10 (m, 2H); LRMS (ESI) 994 ([M+H]$^+$). A solution of 2'-O-(triethylsilyl)-3'-NH-Boc-7-deoxy-7β-thiomethylpaclitaxel (22a) (722 mg, 0.726 mmole) in acetonitrile (14 ml) was cooled in an ice bath and an aqueous solution of hydrochloric acid (1.45 mL, 1.0 N) was added. After 1.17 hr, this was neutralized by adding a saturated aqueous solution of NaHCO$_3$ and then extracted with EtOAc. The organic extracts were washed with brine and dried (Na$_2$SO$_4$). Removal of the solvents followed by radial chromatography (2 mm silica gel plate eluted with mixtures of EtOAc:hexane=7:13 to 11:9) afforded 462 mg (72%) of 3'-NH-Boc-7-deoxy-7β-thiomethylpaclitaxel (23a): $^1$H NMR (CDCl$_3$) 1.13 (s, 3H), 1.17 (s, 3H), 1.29 (s, 9H), 1.72 (s, 3H), 1.88 (s, 3H), 1.94–2.25 (m, 3H), 2.08 (s, 3H), 2.16 (s, 3H), 2.29 (s, 3H), 2.27 (m, 1H), 3.01 (dd, 1H, J=6.4, 11.9 Hz), 3.46 (br s, 1H), 3.76 (d, 1H, J=6.5 Hz), 4.08(d, 1H, J=8.04 Hz), 4.25 (d, 1H, J=8.4 Hz), 4.55 br s, 1H), 4.89 (d, 1H, J=7.8 Hz), 5.25 (br d, 1H, J=8.7 Hz), 5.37 (br d, 1H, J=9.4 Hz), 5.56 (d, 1H, J=6.7 Hz), 6.09 (m, 1H), 6.51 (s, 1H), 7.22–7.57 (m, 8H), 8.02 (m, 2H); LRMS (ESI) 880 ([M+H]$^+$).

EXAMPLE 16

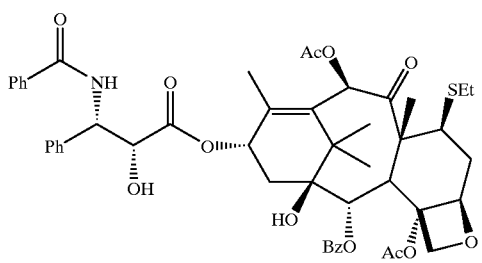

24a

Ethyl iodide (0.057 mL, 1.1 equiv) was added to a solution of 2'-O-(t-butyldimethylsilyl)-7-deoxy-7β-thiopaclitaxel (13a) (637 mg, 0.647 mmole) and 1,8-diazabicyclo[5.4.0]undec-7-ene (0.145 mL, 1.5 equiv) in dry CH$_2$Cl$_2$ (7 mL) at RT and under a N$_2$ atmosphere. After 30 min, the reaction was treated with a saturated solution of NH$_4$Cl and diluted with CH$_2$Cl$_2$. The organic phase was separated, washed with water, and dried (Na$_2$SO$_4$). After the solvent was removed, the residue was dissolved in dry THF (6 mL), cooled in an acetone/ice bath, and tetrabutylammonium fluoride (0.71 mL, 1.0 M in THF, 1.1 equiv) was added. After 15 min, the reaction was quenched by adding a saturated solution of NH$_4$Cl with vigourous stirring. This was extracted with EtOAc (3 times) and the combined organic extracts were washed with brine and dried Na$_2$SO$_4$. Removal of the solvents was followed by radial chromatography (2 mm silica gel plate, eluted with mixtures of EtOAc:hexane=2:3 to 3:2) to afford 441 mg (76%) of 7-deoxy-7β-thioethylpaclitaxel (24a): $^1$H NMR (CDCl$_3$) δ1.16 (s, 3H), 1.22(s, 3H), 1.67 (t, 3H, J=7.4 Hz), 1.70 (s, 3H), 1.86 (s, 3H), 2.03–2.76 (m, 6H), 2.20 (s, 3H), 2.36 (s, 3H), 3.19 (dd, 1H, J=6.5, 11.8 Hz), 3.69 (d, 1H, J=4.8 Hz), 3.82 (d, 1H, J'6.6 Hz), 4.16 (d, 1H, J=8.4 Hz), 4.31 (d, 1H J=8.4 Hz), 4.78 (br s, 1H), 4.93 (d, 1H, J=8.0 Hz), 5.62 (d, 1H, J=6.6 Hz), 5.63 (d, 1H, J=6.6 Hz), 5.78 (dd, 1H, J=2.5, 8.9 Hz), 6.15 (m, 1H), 6.53 (s, 1H), 7.08 (d, 1H, J=8.9 Hz), 7.31–7.63 (m, 11H), 7.75 (m, 2H), 8.09 (m, 2H); LRMS (ESI) 898 ([M+H]$^+$).

EXAMPLE 17

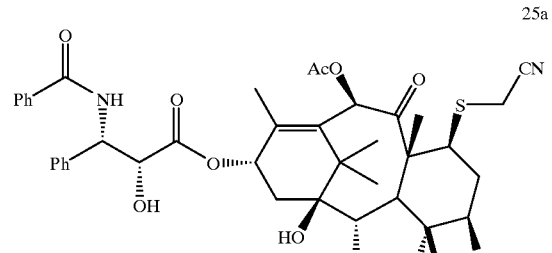

25a

Iodoacetonitrile (0.047 mL, 1.1 equiv) was added to a solution of 7-deoxy-7β-thiopaclitaxel (14a) (514 mg, 0.591 mmole) and 1,8-diazabicyclo[5.4.0]undec-7-ene (0.134 mL, 1.5 equiv) in dry CH$_2$Cl$_2$ (5 mL and under a dry nitrogen atmosphere. After 10 min, the reaction was diluted with CH$_2$Cl$_2$, washed with saturated aqueous NH$_4$Cl, water, and dried (Na$_2$SO$_4$). Removal of the solvents was followed by radial chromatography (1 mm silica gel plate, gradient elution with mixtures of EtOAc:hexane=7:13 to 13:7) afforded 389 mg (72%) of 7-deoxy-7β-thiocyanomethylpaclitaxel (25a): IR (KBr disk) 2248 cm$^{-1}$; $^1$H NMR (CDCl$_3$) δ1.17 (s, 3H), 1.18 (s, 3H), 1.71 (s, 3H), 1.89 (s, 3H), 2.01–2.33 (m, 4H), 2.19 (s, 3H), 2.35 (s, 3H), 2.86 (m, 1H), 3.34 (d, 1H, J=17.5 Hz), 3.42 (d, 1H, J=17.5 Hz), 3.43 (m, 1H), 3.87 (d, 1H, J=6.7 Hz), 4.14 (d, 1H, J=8.5 Hz), 4.30 (d, 1H, J=8.5 Hz), 4.77 (d, 1H, J=2.3 Hz), 4.93 (d, 1H, J=9.0 Hz), 5.63 (d, 1H, J=6.7 Hz), 5.77 (dd, 1H, J=2.0, 88 Hz), 6.15 (m, 1H), 6.47 (s, 1H), 7.07 (d, 1H, J=8.8 Hz), 7.3–7.6 (m, 11H), 7.72 (d, 2H, J=7.7 Hz), 8.08 (d, 2H, J=7.7 Hz); LRMS (negative ESI) 907 ([M–H]$^-$).

EXAMPLE 18

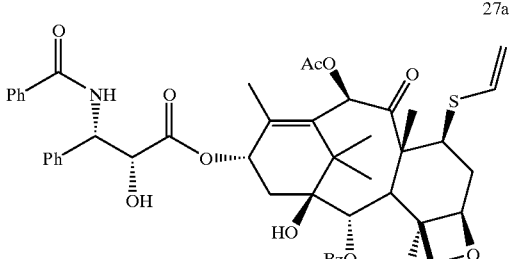

A solution of 2'-O-(t-butyldimethylsilyl)-7-deoxy-7β-thiopaclitaxel (13a) (883 mg, 0.836 mmole) in dry toluene (25 mL) was spared with dry nitrogen for 20 min. 1,8-Diazabicyclo[5.4.0]undec-7-ene (0.187 mL, 1.5 equiv) followed by phenyl vinylsulfoxide (0.117 mL) were added and the solution was left stirring at RT for 6 hr. The reaction was then maintained in a 120° C. oil bath for 22 hr. After cooling to RT, the reaction was diluted with EtOAc, washed with saturated $NH_4Cl$ solution, brine, and then dried ($Na_2SO_4$). Radial chromatography (2 mm silica gel plate eluted with mixtures of EtOAc:hexane=1:4 to 1:3) afforded 679 mg (about 80%) of impure 2'-O-(t-butyldimethylsilyl)-7-deoxy-7β-thiovinylpaclitaxel. This was dissolved in dry THF (3 mL) under dry nitrogen and cooled in an acetone/ice bath. A solution of tetrabutylammonium fluoride (0.74 mL, 1.0 M in THF, 1.1 equiv) was added and after 5 min, the reaction was quenched by adding a saturated solution of $NH_4Cl$ with vigourous stirring. This was extracted with EtOAc (twice) and the combined organic extracts were washed with brine and dried ($Na_2SO_4$). Removal of the solvents followed by radial chromatography (2 mm silica gel plate eluted with with mixtures of EtOAc:hexane=1:2 to 2:3) afforded 345 mg (46% overall) of 7-deoxy-7β-thiovinylpaclitaxel (27a): $^1$H NMR ($CDCl_3+D_2O$) δ1.17 (s, 3H), 1.21 (s, 3H), 1.72 (s, 3H), 1.85 (s, 3H), 2.1–2.3 (m, 3H), 2.18 (s, 3H), 2.37 (s, 3H), 2.75 (m, 1H), 3.44 (dd, 1H, J=6.4, 12.0 Hz), 3.86 (d, 1H, J=6.7 Hz), 4.16 (d, 1H, J=8.4 Hz), 4.31 (d, 1H, J=8.4 Hz), 4.78 (d, 1H, J=2.4 Hz), 4.94 (d, 1H, J=8.1 Hz), 5.27 (br s, 1H), 5.32 (d, 1H, J=5.3 Hz), 5.64 (d, 1H, J=6.7 Hz), 5.78 (dd, 1H, J=9.8, 16.6 Hz, 6.44 (s, 1H), 7.08 (d, 1H, J=8.9 Hz), 7.3–7.6 (m, 11H), 7.74 (d, 2H, J=7.2 Hz), 8.09 (d, 2H, J=87.2 Hz); LRMS (negative ESI) 894 ([M–H]$^-$).

EXAMPLE 19

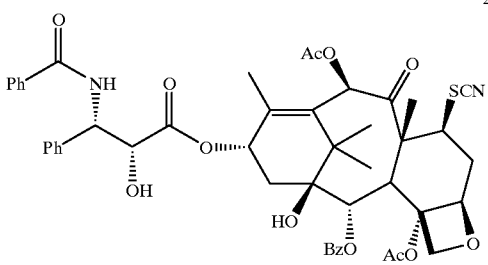

A solution of 2'-O-(t-butyldimethylsilyl)-7-deoxy-7β-thiopaclitaxel (13a) (664 mg, 0.675 mmole) and diisopropyl ethyl amino (0.141 mL, 1.2 equiv) in dry $CH_2Cl_2$ (10 mL) was added to a well-stirred solution of cyanogen bromide (357 mg, 5 equiv) in dry $CH_2Cl_2$ (10 mL) at RT over 3 min. After 15 min, the reaction was treated with an aqueous solution of $Na_2SO_3$ (10%, 20 mL). The organic phase was separated, washed with water, and dried ($Na_2SO_4$). After the solvent was removed, the residue was dissolved in dry THF (6 mL) and cooled in an acetone/ice bath. A solution of tetrabutylammonium fluoride (0.74 mL, 1.0 M in THF, 1.1 equiv) was added. After 5 min, the reaction was quenched by adding a saturated solution of $NH_4Cl$ with vigourous stirring. This was extracted with EtOAc (3 times) and the combined organic extracts were washed with brine and dried $Na_2SO_4$. Removal of the solvents was followed by radial chromatography (2 mm silica gelplate, eluted with mixtures of EtOAc:hexane=8:12 to 11:9) to afford 433 mg (72%) of 7-deoxy-7β-thiocyanatopaclitaxel (28a): IR (KBr disk) 2155 cm$^{-1}$; $^1$H NMR ($CDCl_3$) δ1.16 (s, 3H), 1.20(s, 3H), 1.79 (s, 3H), 1.83 (s, 3H), 2.22 (s, 3H), 2.3–2.4 (m, 3H), 2.95 (m, 1H), 3.64 (d, 1H, J=5.3 Hz), 3.78 (dd, 1H, J=6.5, 11.9 Hz), 3.86 (d, 1H, J=6.8 Hz), 4.17 (d, 1H, J=8.5 Hz), 4.33 (d, 1H J=8.5 Hz), 4.79 (dd 1H, J=2.6, 5.2 Hz), 4.94 (d, 1H, J=7.8 Hz), 5.66 (d, 1H, J=6.8 Hz), 5.77 (dd, 1H, J=2.4, 8.9 Hz), 6.18 (m, 1H), 6.36 (s, 1H), 7.00 (d, 1H, J=8.9 Hz), 7.32–7.64 (m, 11H), 7.74 (d, 2H), 8.10 (d, 2H); LRMS (negative ESI) 893 ([M–H]$^-$).

EXAMPLE 20

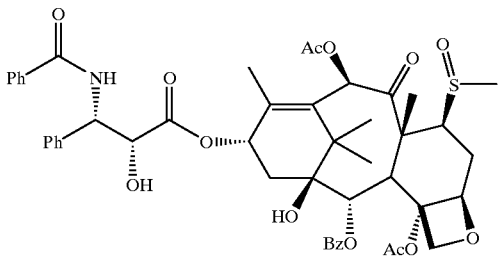

29a and 29b (both sulfoxide diastereomers)

Iodomethane (0.138 mL, 1.1 equiv) was added to a solution of 2'-O-(t-butyldimethylsilyl)-7-deoxy-7β-thiopaclitaxel (13a) (1.99 g, 2.02 mmole) (13a) (1.99 g, 2.02 mmole) and 1,8-diazabicyclo[5.4.0]undec-7-ene (0.459 mL, 1.5 equiv) in dry $CH_2Cl_2$ (20 mL) and under a dry nitrogen atmosphere. After 5 min, the reaction was diluted with EtOAc, washed with saturated aqueous $NH_4Cl$, water, and dried ($Na_2SO_4$). The solvents were removed and the residue was dissolved in $CH_2Cl_2$ (20 mL) and cooled in an acetone/ice bath. A solution of m-chloroperbenzoic acid (435 mg, 80%, 1.05 equiv) in $CH_2Cl_2$ was added. After 30 min, some 10% aqueous $Na_2SO_3$ were added and the reaction was extraced with EtOAc. The organic phase was washed with brine and dried ($Na_2SO_4$). The residue was chromatographed (radial chromatography, 4 mm silica gel plate, eluting with mixtures of EtOAc:hexane) to afford the 2 sulfoxide diastereomers of 2'-O-(t-butyldimethylsilyl)-7-deoxy-7β-methylsulfinylpaclitaxel: a less polar isomer [527 mg; $^1$H NMR ($CDCl_3$)δ-0.30 (s, 3H), -0.06 (s, 3H), 0.79 (s, 9H), 1.18 (s, 3H), 1.21 (s, 3H), 1.81 (s, 3H), 1.86 (s, 3H), 2.12–2.65 (m, 4H), 2.21 (s, 3H), 2.49 (s, 3H), 2.58 (s, 3H), 2.89 (dd, 1H, J=7.6, 11.3 Hz), 3.83 (d, 1H, J=6.6 Hz), 4.15 (d, 1H, J=8.3 Hz), 4.34 (d, 1H J=8.3 Hz), 4.64 (d, 1H, J=2.2 Hz), 5.17 (d, 1H, J=7.9 Hz), 5.70 (m, 2H), 6.23 (m, 1H), 6.28 (s, 1H), 7.06 (d, 1H, J=9.0 Hz), 7.30–7.62(m, 11H), 7.73 (d, 2H), 8.10 (d, 2H)] and a more polar isomer [668 mg; $^1$H NMR ($CDCl_3$) δ-0.27 (s, 3H), 0.00 (s, 3H), 0.82 (s, 9H), 1.20 (s, 3H), 1.22 (s, 3H), 1.82–2.62 (m, 3H), 1.86 (s, 3H), 2.21 (s, 3H), 2.51 (s, 3H), 2.60 (s, 3H), 2.82 (m, 1H), 3.59

(dd, 1H, J=5.8, 12.9 Hz), 3.97 (d, 1H, J=6.5 Hz), 4.27 (d, 1H, J=8.2 Hz), 4.39 (d, 1H J=8.2 Hz), 4.69 (d, 1H, J=2.1 Hz), 5.13 (d, 1H, J=7.8 Hz), 5.74 (m 2H), 6.26 (m, 1H), 6.80 (s, 1H), 7.10 (d, 1H, J=9.0 Hz), 7.31–7.64 (m, 11H), 7.76 (d, 2H), 8.15 (d, 2H)]. The t-butyldimethylsilyl protecting groups were then removed from the individual sulfoxide diastereomers. For the less polar isomer this involved dissolving the compound (509 mg, 0.503 mmole) in dry THF (5 mL), cooling this in an acetone ice bath, and then adding tetrabutylammonium fluoride (0.50 mL, 1.0 M in THF, 1.0 equiv). After 5 min, the reaction was diluted with EtOAc and a solution of $KHSO_4$ (1.4 mL, 1.0 M) was added with vigourous stirring. The organic phase was washed with water (the aqueous washings were back-extracted with EtOAc), brine and dried ($Na_2SO_4$). Removal of the solvents was followed by radial chromatography (2 mm silica gel plate, eluted with mixtures of EtOAc:hexane=4:1 to 100% EtOAc and then a mixture of 2.5% MeOH in EtOAc) to afford 351 mg (78%) of a sulfoxide diastereomer of 7-deoxy-7β-methylsulfinyl-paclitaxel (29a): $^1$H NMR ($CDCl_3$) δ1.17 (s, 3H), 1.20(s, 3H), 1.68 (s, 3H), 1.72 (s, 3H), 2.22 (s, 3H), 2.24–2.63 (m, 6H), 2.39 (s, 3H), 2.46 (s, 3H), 2.85 (dd, 1H, J=7.8, 11.0 Hz), 3.77 (d, 1H, J=6.5 Hz), 4.10 (d, 1H, J=8.3 Hz), 4.30 (d, 1H J=8.3 Hz), 4.75 (d, 1H, J=2.7 Hz), 5.11 (d, 1H, J=8.3 Hz), 5.66 (d, 1H, J=6.5 Hz), 5.75 (dd, 1H, J=2.6, 8.8 Hz), 6.16 (m, 1H), 6.24 (s, 1H), 7.12 (d, 1H, J=8.8 Hz), 7.25–7.63 (m, 11H), 7.74 (m, 2H), 8.09 (m, 2H); LRMS (ESI) 900 ([M+H]$^{30}$). Similar treatment of the more polar silyl ether (651 mg, 643 mmole) afforded 473 mg (82%) of the other sulfoxide diastereomer of 7-deoxy-7β-methylsulfinyl-paclitaxel (29b): $^1$H NMR ($CDCl_3$) δ1.12 (s, 3H), 1.16 (s, 3H),1.86 (s, 3H), 1.76–2.48 (m, 6H), 1.94 (s, 3H), 2.16 (s, 3H), 2.38 (s, 3H), 2.43 (s, 3H), 2.68 (m, 3H), 3.50 (dd, 1H, J=6.1, 12.7 Hz), 3.87 (d, 1H, J=6.5 Hz), 4.20 (d, 1H, J=8.5 Hz), 4.33 (d, 1H J=8.5 Hz), 4.79 (d, 1H, J=2.6 Hz), 5.04 (d, 1H, J=7.9 Hz), 5.67 (d, 1H, J=6.8 Hz), 5.79 (dd, 1H, J=2.4, 8.9 Hz), 6.17 (m, 1H), 6.75 (s, 1H), 7.13 (d, 1H, J=9.0 Hz), 7.31–7.64 (m, 11H), 7.75 (m, 2H), 8.11 (m, 2H); LRMS (ESI) 900 ([M+H]$^+$).

EXAMPLE 21

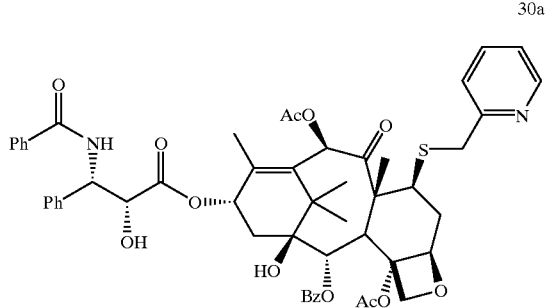

30a 1,8-Diazabicyclo[5.4.0]undec-7-ene (0.360 mL, 3 equiv) was added to an ice-cooled suspension of the hydrochloride salt of 2-picolyl chloride (145 mg, 1.1 equiv) and 2'-O-(t-butyldimethylsilyl)-7-deoxy-7β-thiopaclitaxel (13a) (792 mg, 0.805 mmole) in dry THF (7 mL). After 5 min, the reaction was removed from the bath and allow to stir at RT for 30 min. It was then diluted with 75% EtOAc in hexane and washed with saturated $NH_4Cl$ solution, brine, and dried ($Na_2SO_4$). Radial chromatography (2 mm silica gel plate eluted with mixtures of EtOAc:hexane=3:7 to 3:2) afforded 607 mg 2'-O-(t-butyldimethylsilyl)-7-deoxy-7β-(thio-2-picolyl)-paclitaxel: $^1$H NMR ($CDCl_3$) δ-0.28 (s, 3H), 0.00 (s, 3H), 0.82 (s, 9H), 1.11 (s, 3H), 1.14 (s, 3H), 1.57 (s, 3H), 1.73 (s, 3H), 2.01–2.37 (m, 3H), 2.18 (s, 3H), 2.49 (s, 3H), 2.89 (m, 1H), 3.05 (dd, 1H, J=6.3, 11.3 Hz), 3.68 (d, 1H, J=6.7 Hz), 3.88 (d, 1H, J=13.7 Hz), 3.93 (d, 1H, J=13.7 Hz), 4.14 (d, 1H, J=8.4 Hz), 4.30 (d, 1H J=8.4 Hz), 4.61 (d, 1H, J=1.8 Hz), 4.92 (d, 1H, J=8.1 Hz), 5.63 (m, 2H), 6.10 (m, 1H), 6.22 (s, 1H), 7.04–8.45 (m, 20H). This silyl ether (589 mg, 0.548 mmole) was dissolved in dry THF (6 mL) and cooled in an acetone/ice bath. Tetrabutylammonium fluoride (0.55 mL, 1.0 M in THF, 1.0 equiv) was added and after 5 min, water, and a solution of $KHSO_4$(0.55 mL, 1.0 M) were added with stirring. This was washed with EtOAc (three times) and the combined organic phase were washed with brine and dried ($Na_2SO_4$). Removal of the solvents was followed by radial chromatography (2 mm silica gel plate, eluted with mixtures of EtOAc:hexane=1:1 to 4:1) to afford 447 mg (85%) of 7-deoxy-7β-(thio-2-picolyl)-paclitaxel (30a): $^1$H NMR ($CDCl_3$) δ1.12 (s, 3H), 1.18(s, 3H), 1.45 (s, 3H), 1.72 (s, 3H), 1.97–2.63 (m, 3H), 2.20 (s, 3H), 2.82 (m, 1H), 3.00 (dd, 1H, J=6.7, 11.5 Hz), 3.64 (d, 1H, J=6.7 Hz), 3.72 (d, 1H, J=4.7 Hz), 3.83 (d, 1H, J=13.8 Hz), 3.92 (d, 1H, J=13.8 Hz), 4.12 (d, 1H, J=8.5 Hz), 4.28 (d, 1H J=8.5 Hz), 4.75 (dd, 1H, J=2.8, 4.45 Hz), 4.86 (d, 1H, J=8.0 Hz), 5.58 (d, 1H, J=6.6 Hz), 5.76 (dd, 1H, J=2.4, 8.9 Hz), 6.07 (m, 1H), 6.23 (s, 1H), 7.05 (d, 1H, J=8.9 Hz), 7.10–8.51 (m, 19H); LRMS (ESI) 961 ([M+H]$^+$).

EXAMPLE 22

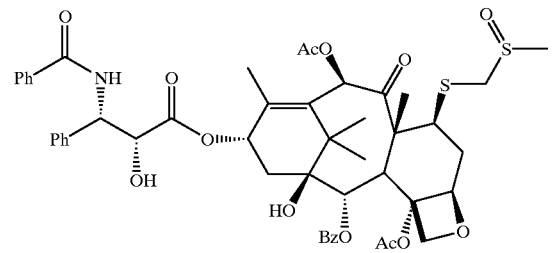

31a and 31b (mixture of sulfoxide diasteromers)

Chloromethyl methylsulfide (0.435 mL, 3 equiv) was added to a solution of 2'-O-(t-butyldimethylsilyl)-7-deoxy-7β-thiopaclitaxel (14a) (1.48 g, 1.50 mmole) and 1,8-diazabicyclo[5.4.0]undec-7-ene (0.912 mL, 4 equiv) in dry benzene (15 mL) and under a dry nitrogen atmosphere. After 5 min, the reaction was diluted with EtOAc, washed with saturated aqueous $NH_4Cl$, brine, and dried ($Na_2SO_4$). The solvents were removed and the residue was chromatographed (silica gel column chromatography; eluting with mixtures of EtOAc:hexane=1:4 to 7:13) to afford 1.08 gm (70%) of O-(t-butyldimethylsilyl)-7-deoxy-7β-thiomethylthiomethylpaclitaxel: $^1$H NMR ($CDCl_3$) δ-0.28 (s, 3H), -0.00 (s, 3H), 0.82 (s, 9H), 1.25 (s, 3H), 1.21 (s, 3H), 1.80 (s, 3H), 2.06–2.48 (m, 3H), 2.08 (s, 3H), 2.21 (s, 3H), 2.23 (s, 3H), 2.61 (s, 3H), 2.81 (m, 1H), 2.54 (dd, 1H, J=6.4, 11.7 Hz), 3.65 (d, 1H, J=14.3 Hz), 3.74 (d, 1H, J=14.3 Hz), 3.93 (d, 1H J=6.8 Hz), 4.23 (d, 1H, J=8.4 Hz), 4.37 (d, 1H, J=8.4 Hz), 4.70 (d, 1H, J=2.1 Hz), 5.71 (d, 1H, J=6.8 Hz), 5.76 (m, J=1.8, 8.9 Hz), 6.2 (m, 1H), 6.52 (s, 1H), 7.09 (d, 1H, J=8.9 H), 7.31–8.106 (m, 15H); LRMS (negative ESI) 1042 ([M–H]$^-$). A solution of m-chloroperbenzoic acid (203 mg, 80%, 1equiv) in $CH_2Cl_2$ was added to a solution of O-(t-butyldimethylsilyl)-7-deoxy-7β-thiomethylthiomethylpaclitaxel (983 mg, 0.942 mmole) in $CH_2Cl_2$ (15 mL) in an acetone/ice bath. After 20 min, some 10% aqueous Na$_2$SO$_3$ was added and the reaction was extracted with a mixture of EtOAc:hexane=1:1. The organic phase was washed with saturated NaHCO$_3$ solution (three times), brine and dried (Na$_2$SO$_4$). Removal of the solvents left a white solid which was taken directly and dissolved in dry THF (8 mL). This was cooled it an acetone ice bath and tetrabutylammonium fluoride (0.50 mL, 1.0 M in THF, 1.0 equiv). After 15 min, the reaction was diluted with EtOAc and a solution of KHSO$_4$ (2 mL, 1.0 M) and water were added with stirring. The organic phase was separated, washed with brine, and dried (Na$_2$SO$_4$). Removal of the solvents was followed by silica gel column chromatography (eluting with mixtures of EtOAc:hexane=1:1 to 100% EtOAc) to give 360 mg (40%) of an approximately 3:1 mixture of chromatographically homogeneous sulfoxide diastereomers of 7-deoxy-7β-methylsulfinylmethylthiopaclitaxel (31a and 31b): $^1$H NMR (CDCl$_3$) δ1.11–2.91 (m, 25H, 3.46–4.22 (m, 6H), 4.71 (d, 1H, J≦2.8 Hz), 4.86 (br d, 1H, J=7.8 Hz), 5.57 (d, 1H, J=6.7 Hz), 5.71 (dd, 1H, J=2.5, 8.5 Hz), 6.08 (m, 1H), 6.40 (s, 0.75H), 6.52 (s, 0.25H), 7.23–8.04 (m, 16H); LRMS (negative ESI) 944 ([M−H]$^-$).

EXAMPLE 23

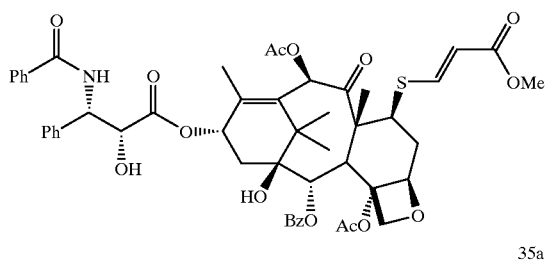

34a

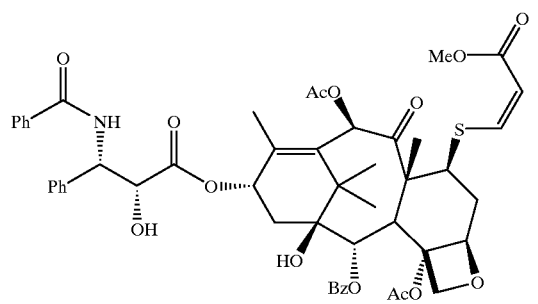

35a

Methyl propiolate (0.159 mL, 1.5 equiv) was added to an ice cooled solution of 2'-O-(t-butyldimethylsilyl)-7-deoxy-7β-thiopaclitaxel (13a) (1.17 g, 1.19 mmole) and 1,8-diazabicyclo[5.4.0]undec-7-ene (0.017 mL, 0.1 equiv) in dry CH$_2$Cl$_2$ (25 mL). After 30 min, the reaction was diluted with EtAOc and wash with saturated aqueous NH$_4$Cl, brine, and dried (Na$_2$SO$_4$). The solvents were removed and the residue was chromatographed (silica gel column; eluting with mixtures of EtOAc:hexane=1.4 to 7:13) to separate the E and Z methyl acrylate isomers. This afforded 399 mg of a less polar isomer and 563 mg of a polar isomer of O-(t-butyldimethylsilyl)-7-deoxy-7β-(3-methylacrylate)paclitaxel. The less polar isomer (390 mg, 0.366 mmole) was dissolved in dry THF (4 mL) and cooled in an acetone/ice bath. Tetrabutylammonium fluoride (0.36 mL, 1.0 M in THF, 1.0 equiv) was added and after 5 min, the reaction was diluted with EtOAc and a solution of KHSO$_4$(0.73 mL, 1.0 M) and water were added with stirring. The organic phase was separated, washed with brine, and dried (Na$_2$SO$_4$). Removal of the solvents followed by silica gel column chromatography (eluting with a mixtures of EtOAc:hexane: CH$_2$Cl$_2$=7:13:9:11) gave 210 mg (60%) of the E isomer of 7-deoxy-7β-thio-(3-methylacrylate)paclitaxel (34a): $^1$H NMR (CDCl$_3$) δ1.12 (s, 3H), 1.14 (s, 3H), 1.70 (s, 3H), 1.79 (s, 3H), 2.12 (s, 3H), 2.04–2.28 (m, 3H), 2.33 (s, 3H), 2.36 (s, 3H), 2.70 (m, 1H), 3.26 (dd, 1H, J=6.5, 12.1 Hz), 3.66 (s, 3H), 3.83 (d, 1H, J=6.7 Hz), 4.11 (d, 1H, J=8.5 Hz), 4.27 (d, 1H J=8.5 Hz), 4.75 (d, 1H, J=2.2 Hz), 4.88 (d, 1H, J=7.9 Hz), 5.59 (d, 1H, J=6.8 Hz), 5.73 (dd, 1H, J=2.4, 8.9 Hz), 5.83 (d, 1H, J=15.2 Hz), 6.11 (m, 1H), 6.29 (s, 1H), 7.02 (d, 1H, J=8.9 Hz), 7.51–8.09 (m, 16H); LRMS (ESI) 952 ([M+H]$^+$). Similar treatment of the more polar isomer (563 mg, 528 mmole) afforded 357 mg (71%) of the Z isomer of 7-deoxy-7β-thio-(3-methylacrylate)paclitaxel (35a): $^1$H NMR (CDCl$_3$) δ1.11 (s, 3H), 1.15 (s, 3H), 1.64 (s, 3H), 1.70 (s, 3H), 1.80 (s, 3H), 2.09 (s, 3H), 2.14–2.36 (m, 3H), 2.32 (s, 3H), 2.60 (m, 1H), 3.21 (dd, 1H, J=6.7, 12.0 Hz), 3.62 (m, 1H), 3.64 (s, 3H), 3.80 (d, 1H, J=6.6 Hz), 4.10 (d, 1H, J=8.5 Hz), 4.25 (d, 1H, J=8.5 Hz), 4.71 (dd, 1H, J=2.4, 5.0 Hz), 4.86 (d, 1H, J=7.7 Hz), 5.60 (d, 1H, J=6.6 Hz), 5.72 (dd, 1H, J=2.5, 8.9 Hz), 5.81 (d, 1H, J=10.1 Hz), 6.10 (m, 1H), 6.35 (s, 1H), 6.86 (d, 1H, J=10.1 Hz), 7.01 (d, 1H, J=8.9 Hz), 7.27–8.05 (m, 15H); LRMS (negative ESI) 952 ([M−H]$^-$)

The compounds of this invention exhibit antitumor activities in in vivo and/or in vitro models. For example, the following test describes the in vitro test used to evaluate some representative compounds of this invention.

Cytoxicity (In-Vitro)

Cytoxicity was assessed in HCT-116 human colon carcinoma cells by MTS (3-(4,5-dimethylthiazol-2-yl)-5-(3-carboxymethoxyphenyl)-2-(4-sulphenyl)-2H-tetrazolium, inner salt) assay as reported in T. L. Riss, et al., "Comparison of MTT, XTT, and a novel tetrazolium compound MTS for in vitro proliferation and chemosensitivity assays.", Mol. Biol. Cell 3 (Suppl.):184a, 1992. Cells were plated at 4,000 cell/well in 96 well microtiter plates and 24 hours later drugs were added and serial diluted. The cells were incubated at 37° C. for 72 hours at which time the tetrazolium dye, MTS at 333 μg/ml (final concentration), in combination with the electron coupling agent phenazine methosulfate at 25 μM (final concentration) was added. A dehydrogenase enzyme in live cell reduces the MTS to a form that absorbs light at 492 nM which can be quantitated spectrophotometrically. The greater the absorbance the greater the number of live cells. The results are expressed as an IC$_{50}$, which is the drug concentration required to inhibit cell proliferation (i.e. absorbance at 450 nM) to 50% of that of untreated control cells. The IC$_{50}$ values for compounds evaluated in this assay are presented in Table II.

TABLE II

| Compound | IC$_{50}$ (nM) HCT 116 |
| --- | --- |
| 5a (Example 2) | 13.1 |
| 7a (Example 4) | 72.3 |
| 9a (Example 6) | 2.99 |
| 14a (Example 10) | 13.5 |
| 16a (Example 12) | 0.50 |
| 18a (Example 13) | 0.20 |
| 20a (Example 14) | 0.82 |
| 22a (Example 15) | 0.30 |
| 24a (Example 16) | 4.02 |
| 25a (Example 17) | <0.04 |
| 27a (Example 18) | 1.2 |

TABLE II-continued

| Compound | IC$_{50}$ (nM) HCT 116 |
| --- | --- |
| 28a (Example 19) | 1.8 |
| 29a (Example 20) | 3.99 |
| 29b (Example 20) | 12.06 |
| 30a (Example 21) | 1.12 |
| 31a&b (Example 22) | 6.48 |
| 34a (Example 23) | 6.97 |
| 35a (Example 23) | 1.76 |
| paclitaxel | 1.71–2.28 |

Another aspect of the instant invention concerns a method for inhibiting human and/or other mammalian tumors which comprises administering to a tumor bearing host an antitumor effective amount of a compound of formula I.

For treating a variety of tumors, the compound of formula I of the present invention may be used in a manner similar to that of paclitaxel, e.g. see Physician's Desk Reference 49th Edition, Medical Economics, p 682, 1995. The dosage, mode and schedule of administration for the compound of this invention are not particularly restricted; an oncologist skilled in the art of cancer treatment will be able to ascertain, without undue experimentation, an appropriate treatment protocol for administering the compound of the present invention. Thus the compound of formula I may be administered via any suitable route of administration, parenterally or orally. Parenteral administration includes intravenous, intraperitoneal, intramuscular, and subcutaneous administration.

The doses utilized to implement the methods in accordance with the invention are the ones that make it possible to administer prophylactic treatment or to evoke a maximal therapeutic response. The doses vary, depending on the type of administration, the particular product selected, and the personal characteristics of the subject to be treated. In general, the doses are the ones that are therapeutically effective for the treatment of disorders caused by abnormal cell proliferation. The products in accordance with the invention can be administered as often as necessary in order to obtain the desired therapeutic effect. Some patients may respond rapidly to relatively high or low doses, and then required mild maintenance or no maintenance dose at all. Via the iv route, the dosage may be, for example, in the range of about 20 to about 500 mg/m$^2$ over 1 to 100 hours. Via the oral route, the dosage may be in the range of 5–1000 mg/kg/day of body weight. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical formulations (compositions) containing an antitumor effective amount of compound of formula I in combination with one or more pharmaceutically acceptable carriers, excipients, diluents or adjuvants. The compositions can be prepared in accordance with conventional methods. Examples of formulating paclitaxel or derivatives thereof may be found in, for example, U.S. Pat. Nos. 4,960,790 and 4,814,470, and such examples may be followed to formulate the compound of this invention. For example, compound of formula I may be formulated in the form of tablets, pills, powder mixtures, capsules, injectables, solutions, suppositories, emulsions, dispersions, food premix, and in other suitable forms. It may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manital, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

What is claimed is:

1. A compound of formula I, or a pharmaceutically acceptable salt thereof

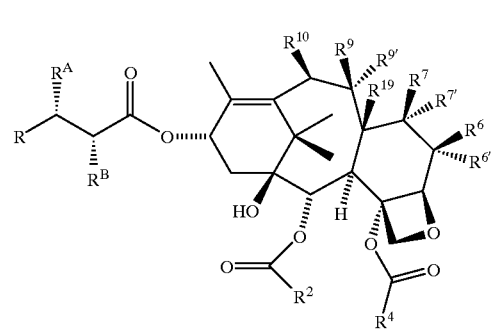

wherein R is hydrogen, $C_{1-6}$ alkyl, $C_{2-6}$ alkenyl, $C_{2-6}$ alkynyl, or —$Z^1$—$R^3$;

$Z^1$ is a direct bond, $C_{1-6}$ alkyl, or —O-$C_{1-6}$ alkyl;

$R^3$ is aryl, substituted aryl, $C_{3-6}$ cycloalkyl, $C_{3-6}$ cycloalkenyl, cyclic 3–7 membered ring consisting of either one or two heteroatoms, or heteroaryl;

$R^A$ is —NHC(O)R, —NHC(O)OR, —NHC(O)NHR, —NHC(O)N(R)$_2$, —NHS(O)$_k$R, —NHP(=O)(OR)$_2$ or —NHP=S(OR)$_2$, where k is 1 or 2;

$R^B$ is hydroxy, fluoro, —OC(OR)R$^x$, —OC(O)OR$^x$, OP(O)(OH)$_2$, OCH$_2$OP(O)(OH)$_2$, —OCH$_2$OCH$_2$OP (=O)(OH)$_2$, —(OCH)$_2$)$_m$OC=OCH$_2$NHR$^x$, —(OCH$_2$)$_m$OC(=O)CH(R")NR'$_6$R'$_7$ where m is 0–3, —OCOCH$_2$CH$_2$NH$_3^+$HCOO$^-$, —OCOCH$_2$CH$_2$COOH, —OCO(CH$_2$)$_3$COOH,—OC (O)(CH$_2$)$_n$NR$^F$R$^G$, where n is 0–3, —OC(O)CH$_2$CH$_2$C (O)OCH$_2$CH$_2$OH or —OC(O)—Z—C(O)—R'; Z is ethylene (—CH$_2$CH$_2$—), propylene (—CH$_2$CH$_2$CH$_2$—), —CH=CH—, 1,2-cyclohexane or 1,2-phenylene;

R' is —OH, —NR'$_2$R'$_3$, —OR'$_3$, —SR'$_3$, or —OCH$_2$C(O) NR'$_4$R'$_5$;

R'$_2$ is —H or —CH$_3$;

R'$_3$is —(CH$_2$)$_j$NR'$_6$R'$_7$ or (CH$_2$)$_n$N$^+$R'$_6$R'$_7$R'$_8$X$^-$, where j is 1–3;

R'$_4$ is —H or —C$_1$–C$_4$ alkyl;

R'$_5$ is —H, —C$_1$–C$_4$ alkyl, benzyl, hydroxyethyl, —CH$_2$CO$_2$H or dimethylaminoethyl;

R'$_6$ and R'$_7$ are independently —H, —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group;

R'$_8$ is —CH$_3$, —CH$_2$CH$_3$ or benzyl;

X$^-$ is halide;

R$^F$ and R$^G$ are independently —H or —C$_1$-C$_3$ alkyl, or R$^F$ and R$^G$ taken together with the nitrogen of NR$^F$R$^G$ form a pyrrolidino, piperidino, morpholino or N-methylpiperizino groups;

R" is —H, —CH$_3$, —CH$_2$CH(CH$_3$)$_2$, —CH(CH$_3$)CH$_2$CH$_3$, —CH(CH$_3$)$_2$, —CH$_2$phenyl, —(CH$_2$)$_3$NH$_2$, —(CH$_2$)$_4$NH$_2$, —CH$_2$CH$_2$COOH, —(CH$_2$)$_3$NHC(=NH)NH$_2$, the residue of the amino acid proline, —OC(O)CH=CH$_2$, —C(O)CH$_2$CH$_2$C(O)NHCH$_2$CH$_2$SO$_3$—Y+ or —OC(O)CH$_2$CH$_2$C(O)NHCH$_2$CH$_2$CH$_2$SO$_3$—Y+;

Y+ is Na+ or N+(Bu)$_4$;

R$^2$ is aryl or substituted aryl;

R$^4$ is —C$_{1-6}$ alkyl, —OC—C$_{1-6}$ alkyl, or —C$_{3-6}$ cycloalkyl;

R$^6$ and R$^{6'}$ are independently hydrogen, hydroxy, C$_{1-6}$ alkyl, —SH, —S—R$^W$, halo, or together R$^6$ and R$^{6'}$ form a ketone;

R$^7$ and R$^{7'}$ are independently hydrogen, mercapto, —S—R$^W$, —S(R$^W$)$_2$$^+$K$^-$, —S(O)—R$^W$, —S(O)$_2$R$^W$, —S(O)$_2$OH and the corresponding salts, —S(O)$_2$NHR$^x$, —S(O)$_2$N(R$^x$)$_2$, —S—S—R$^W$, —S—S—R$^3$, —S(CH$_2$)$_a$R$^3$, where a is 0–4, —S—CN, —S(O)—CN, —S(O)$_2$—CN, —SC(O)R$^x$, —SC(O)OR$^x$, —SC(S)R$^x$, —SC(S)SR$^x$, —SC(O)NHR$^x$, —SC(OH)NR'$_6$R'$_7$, —SCH$_2$OR, —SC(R$^x$)$_2$OR, —SCHR$^x$OR, —SCH$_2$OCH$_2$OCH$_3$, —SCH$_2$SR, —SC(R$^x$)$_2$SR, —SCHR$^x$SR, —SCOCH$_2$CH$_2$NH$_3$$^+$HCOO$^-$, —SCOCH$_2$CH$_2$COOH, —SCO(CH$_2$)$_3$COOH, OC(O)(CH$_2$)$_n$NR$^F$R$^G$, where n is 0–3, with the proviso that n is not 1 when R$^F$ and R$^G$ are each methyl, —SC(O)—Z—C(O)—R', —SC(O)CH$_2$CH$_2$C(O)OCH$_2$CH$_2$OH, —S(O)$_b$CH$_2$CN, where is b is 0–2, —SCH$_2$C(O)C$_{1-6}$ alkyl, —SCH=C(X)(Y), —S(SCH$_2$)$_r$R$^2$, where r is 1–4, or —S(CH$_2$)S(O)$_t$C$_{1-6}$ alkyl, where t is 0–2, with the proviso that both of R$^7$ and R$^{7'}$ cannot simultaneously be hydrogen;

X and Y are independently hydrogen, COOR$^a$, C(O)R$^a$, R$^a$, CN, aryl or heteroaryl, where R$^a$ is C$_{1-6}$ alkyl;

K is Br$^-$, Cl$^-$, I$^-$, CH$_3$SO$_3$—, BF$_4$—, CF$_3$COO—, CH$_3$COO— or CF$_3$SO$_2$—;

R$^9$ and R$^{9'}$ are independently hydrogen or hydroxy or together R$^9$ and R$^{9'}$ form a ketone; provided R$^{9'}$ and R$^{7'}$ taken together can form part of a ring joined by —CH$_2$S(O)$_q$— in which the carbon is attached at R$^{9'}$ and the sulfur at R$^{7'}$ and where q is 0–2, R$^9$ is —OH, and R$^7$ is hydrogen; further provided R$^{9'}$ and R$^{7'}$ taken together can form part of a ring joined by =CHS(O)$_q$— in which the carbon is attached at R$^9$ and R$^{9'}$ to form a double bond and the sulfur at R$^{7'}$ and where q is 0–2, and R$^7$ is hydrogen;

R$^{10}$ is hydrogen, hydroxy, —OC(O)R$^x$, —OC(O)OR$^x$, —O—C$_{1-6}$ alkyl, —OCH$_2$OCH$_3$, —OCH$_2$OCH$_2$OCH$_3$, —OCH$_2$OCH$_2$OCH$_3$, —OCH$_2$OCH$_2$CH$_2$OCH$_3$—OCH$_2$OCH$_2$CH$_2$OH, —OCH$_2$SR, —OCH$_2$OCH$_2$SCH$_3$, —OC(O)NR'$_6$R'$_7$, C$_{1-6}$ alkyl, —(CH$_2$)$_3$C(O)R$^x$, —(CH$_2$)$_3$C(O)OR$^x$, —(CH$_2$)$_3$CN, —OP(O)(OH)$_2$, —OCH$_2$OP(O)(OH)$_2$, —OCH$_2$OCH$_2$OP(O)(OH$_2$, —(OCH$_2$)$_n$OC=OCH$_2$NHR$^x$, —(OCH$_2$)$_n$OC(=O)CH$_{(R'')}$NR'$_6$R'$_7$, where n is 0–3, —OCOCH$_2$CH$_2$NH$_3$$^+$HCOO$^+$, —OCOCH$_2$CH$_2$COOH, —OCO(CH$_2$)$_3$COOH, —OC(O)—Z—C(O)—R', —OC(O)(CH$_2$)$_n$NR$^F$R$^G$ where n is 0–3, or —OC(O)CH$_2$CH$_2$C(O)OCH$_2$CH$_2$OH;

R$^{19}$ is methyl or hydroxymethyl;

R$^X$ is C$_{1-6}$ alkyl, C$_{2-6}$ alkenyl, C$_{2-6}$ alkynyl, C$_{3-6}$ cyclo alkyl any of which groups can be optionally substituted with one to six of the same or different halogen atoms or with one or more hydroxy groups; and R$^W$ is C$_{1-6}$ alkyl any of which groups can be optionally substituted with one to six of the same or different halogen atoms or with one or more hydroxy groups or with one or more carboxy groups or with one or more carboxy C$_{1-6}$ alkyl esters or with one or more mercapto groups.

2. A compound of claim 1, wherein

R is 2-furanyl (2-furyl), 2-thienyl, 3-furanyl (3-furyl), 3-thienyl, phenyl, substituted phenyl, C$_{3-6}$ alkyl, C$_{3-6}$ alkenyl, C$_{3-6}$ cycloalkyl or C$_{3-6}$ cycloalkenyl;

R$^A$ is —NHC(O)Ph, wherein Ph is substituted or unsubstituted, —NHC(O)O(C$_{1-6}$ alkyl), —NHC(O)OCH$_2$Ph, NHC(O)-heterocycle, —NHC(O)NHR or —NHC(O)N(R)$_2$.

3. A compound of claim 2, wherein

R is phenyl, mono or di-substituted phenyl, C$_{3-6}$ cycloalkyl, C$_{3-6}$ alkyl, C$_{3-6}$ alkenyl or C$_{3-6}$ cycloalkenyl;

R$^2$ is phenyl or substituted phenyl;

R$^B$ is hydroxy, —OC(O)R$^x$, —OC(O)OR$^x$, OP(O)(OH)$_2$, OCH$_2$OP(O)(OH)$_2$, —OCH$_2$OCH$_2$OP(=O)(OH)$_2$, —(OCH$_2$)$_m$OC=OCH$_2$NHR$^x$, —(OCH$_2$)$_m$OC(=O)CH(R")NR'$_6$R'$_7$ where m is 0–3, —OCOCH$_2$CH$_2$NH$_3$$^+$HCOO$^-$, —OCOCH$_2$CH$_2$COOH, —OCO(CH$_2$)$_3$COOH,—OC(O)(CH$_2$)$_n$NR$^F$R$^G$, where n is 0–3, —OC(O)CH$_2$CH$_2$C(O)OCH$_2$CH$_2$OH or —OC(O)—Z—C(O)—R';

R$^{10}$ is hydrogen, hydroxy, —OC(O)R$^x$, —OC(O)OR$^x$, —O—C$_{1-6}$ alkyl or —OCH$_2$OCH$_3$.

4. A compound of claim 3, wherein

R$^A$ is —NHC(O)O-(C$_{1-6}$)alkyl, —NHC(O)OCH$_2$Ph, —NHC(O)Ph or NHC(O)-2-furyl;

R$^B$ is hydroxy;

R$_4$ is C$_{1-3}$ alkyl, —O-C$_{1-2}$ alkyl or cyclopropyl;

R is phenyl, 4-methylphenyl, 4-chlorophenyl, 4-bromophenyl, 4-fluorophenyl or 4-methoxphenyl;

R$^6$ and R$^{6'}$ are independently hydrogen; and

R$^{19}$ is methyl.

5. A compound of claim 4, wherein

R$^A$ is —NHC(O)OtBu or —NYC(O)Ph;

R is phenyl; and

R$^2$ is phenyl.

6. A compound of claim 5, wherein

R$^4$ is —CH$_3$; and

R$^{9'}$ and R$^{7'}$ taken together can form part of a ring joined by —CH$_2$S(O)$_q$ in which the carbon is attached at R$^{9'}$ and the sulfur at R$^{7'}$ and where q is 0–2, R$^9$ is —OH, and R$^7$ is hydrogen.

7. A compound of claim 6, wherein

R$^A$ is —NYC(O)Ph; and

R$^{9'}$ and R$^{7'}$ taken together can form part of a ring joined by —CH$_2$S(O)$_2$ in which the carbon is attached at R$^{9'}$ and the sulfur at R$^{7'}$ and where R$^9$ is —OH, and R$^7$ is hydrogen.

8. A compound of claim 6, wherein $R^A$ is —NHC(O)OtBu; and $R^{9'}$ and $R^{7'}$ taken together can form part of a ring joined by —CH$_2$S(O)$_2$ in which the carbon is attached at $R^{9'}$ and the sulfur at $R^{7'}$ and where $R^9$ is —OH, and $R^7$ is hydrogen.

9. A compound of claim 4, wherein $R^2$ is phenyl; and $R^9$ and $R^{9'}$ taken together can form a ketone.

10. A compound of claim 9, wherein $R^7$ is mercapto, —S—$R^W$, —S(O)—$R^W$, —S(O)$_2R^W$, —S—CN, —SC(O)$R^x$, —SC(O)O$R^x$, —SC(S)$R^x$, —SC(S)S$R^x$, —SC(O)NH$R^x$, —SC(O)NR'$_6$R'$_7$, —SCH$_2$OR, —SC(R$^x$)$_2$OR, —SCHR$^x$OR, —SCH$_2$OCH$_2$OCH$_3$, —SCH$_2$SR, —SC(R$^x$)$_2$SR or —SCHR$^x$SR; and $R^{7'}$ is hydrogen.

11. A compound of claim 10, wherein $R^4$ is CH$_3$.

12. A compound of claim 11, wherein $R^A$ is —NHC(O)OtBu or —NHC(O)Ph; and

R is phenyl.

13. A compound of claim 12, wherein $R^A$ is —NHC(O)Ph; and $R^7$ is mercapto.

14. A compound of claim 12, wherein $R^A$ is —NHC(O)Ph; and $R^7$ is —SCH$_2$OCH$_3$.

15. A compound of claim 12, wherein $R^A$ is —NHC(O)Ph; and $R^7$ is —SCH$_2$OCH$_3$.

16. A compound of claim 12, wherein $R^A$ is —NHC(O)Ph; and $R^7$ is —SCH$_3$.

17. A baccatin intermediate compound of formula II

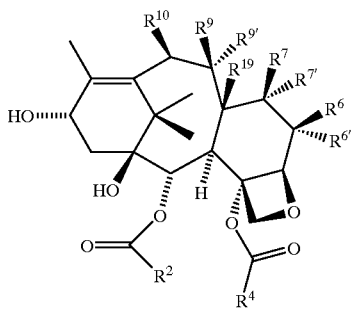

II wherein R is hydrogen, C$_{1-6}$alkyl, C$_{2-6}$alkenyl, C$_{2-6}$alkynyl, or —Z$^1$—R$^3$;

$Z^1$ is a direct bond, C$_{1-6}$alkyl, or —O-C$_{1-6}$alkyl;

$R^3$ is aryl, substituted aryl, C$_{3-6}$ cycloalkyl, C$_{3-6}$ cycloalkenyl, cyclic 3–7 membered ring containing either one or two heteroatoms, or heteroaryl;

Z is ethylene (—CH$_2$CH$_2$—), propylene (—CH$_2$CH$_2$CH$_2$—), —CH=CH—, 1,2-cyclohexane or 1,2-phenylene;

R' is —OH, —NR'$_2$R'$_3$, —OR'$_3$, —SR'$_3$, or —OCH$_2$C(O)NR'$_4$R'$_5$;

R'$_2$ is —H or —CH$_3$;

R'$_3$ is —(CH$_2$)$_j$NR'$_6$R'$_7$ or (CH$_2$)$_n$N$^+$R'$_6$R'$_7$R'$_8$X$^-$, where j is 1–3;

R'$_4$ is —H or —C$_1$–C$_4$ alkyl;

R'$_5$ is —H, —C$_1$–C$_4$ alkyl, benzyl, hydroxyethyl, —CH$_2$CO$_2$H or dimethylaminoethyl;

R'$_6$ and R'$_7$ are independently —H, —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group;

R'$_8$ is —CH$_3$, —CH$_2$CH$_3$ or benzyl;

X$^-$ is halide;

$R^F$ and $R^G$ are independently —H or —C$_1$-C$_3$ alkyl, or $R^F$ and $R^G$ taken together with the nitrogen of NR$^F$R$^G$ form a pyrrolidino, piperidino, morpholino or N-methylpiperizino groups;

R" is —H, —CH$_3$, —CH$_2$CH(CH$_3$)$_2$, —CH(CH$_3$)CH$_2$CH$_3$, —CH(CH$_3$)$_2$, —CH$_2$phenyl, —(CH$_2$)$_3$NH$_2$, —(CH$_2$)$_4$NH$_2$, —CH$_2$CH$_2$COOH, —(CH$_2$)$_3$NHC(=NH)NH$_2$, the residue of the amino acid proline, —OC(O)CH=CH$_2$, —C(O)CH$_2$CH$_2$C(O)NHCH$_2$CH$_2$SO$_3$—Y+ or —OC(O)CH$_2$CH$_2$C(O)NHCH$_2$CH$_2$CH$_2$SO$_3$—Y+;

Y+ is Na+ or N+(Bu)$_4$;

$R^2$ is aryl or substituted aryl;

$R^4$ is —C$_{1-6}$ alkyl, —OC—C$_{1-6}$ alkyl, or —C$_{3-6}$ cycloalkyl;

$R^6$ and $R^{6'}$ are independently hydrogen, hydroxy, C$_{1-6}$ alkyl, —SH, —S—$R^W$, halo, or together $R^6$ and $R^{6'}$ form a ketone;

$R^7$ and $R^{7'}$ are independently hydrogen, mercapto, —S—$R^W$, —S(R$^W$)$_2$$^+$K$^-$, —S(O)—$R^W$, —S(O)$_2R^W$, —S(O)$_2$OH and the corresponding salts, —S(O)$_2$NHR$^x$, —S(O)$_2$N(R$^x$)$_2$, —S—S—$R^W$, —S—S—$R^3$, —S(CH$_2$)$_a$R$^3$, where a is 0–4, —S—CN, —S(O)—CN, —S(O)$_2$—CN, —SC(O)R$^x$, —SC(O)OR$^x$, —SC(S)R$^x$, —SC(S)SR$^x$, —SC(O)NHR$^x$, —SC(OH)NR'$_6$R'$_7$, —SCH$_2$OR, —SC(R$^x$)$_2$OR, —SCHR$^x$OR, —SCH$_2$OCH$_2$OCH$_3$, —SCH$_2$SR, —SC(R$^x$)$_2$SR, —SCHR$^x$SR, —SCOCH$_2$CH$_2$NH$_3$$^+$HCOO$^-$, —SCOCH$_2$CH$_2$COOH, —SCO(CH$_2$)$_3$COOH, —OC(O)(CH$_2$)$_n$NR$^F$R$^G$, where n is 0–3, —SC(O)—Z—C(O)—R', —SC(O)CH$_2$CH$_2$C(O)OCH$_2$CH$_2$OH, —S(O)$_b$CH$_2$CN, where is b is 0–2, —SCH$_2$C(O)C$_{1-6}$ alkyl, —SCH=C(X)(Y), —S(SCH$_2$)$_r$R$^2$, where r is 1–4, or —S(CH$_2$)S(O)$_tC_{1-6}$ alkyl, where t is 0–2, with the proviso that both of $R^7$ and $R^{7'}$ cannot simultaneously be hydrogen;

X and Y are independently hydrogen, COOR$^a$, C(O)R$^a$, R$^a$, CN, aryl or heteroaryl, where R$^a$ is C$_{1-6}$ alkyl;

K is Br$^-$, Cl$^-$, I$^-$, CH$_3$SO$_3$—, BF$_4$—, CF$_3$COO—, CH$_3$COO— or CF$_3$SO$_2$—;

$R^9$ and $R^{9'}$ are independently hydrogen or hydroxy or together $R^9$ and $R^{9'}$ form a ketone; provided $R^{9'}$ and $R^{7'}$ taken together can form part of a ring joined by —CH$_2$S(O)$_q$— in which the carbon is attached at $R^{9'}$ and the sulfur at $R^{7'}$ and where q is 0–2, $R^9$ is —OH, and $R^7$ is hydrogen; further provided $R^{9'}$ and $R^{7'}$ taken together can form part of a ring joined by —CHS(O)$_q$— in which the carbon is attached at $R^9$ and $R^{9'}$ to form a double bond and the sulfur at $R^7$ and where q is 0–2, and $R^7$ is hydrogen;

$R^{10}$ is hydrogen, hydroxy, —OC(O)$R^x$, —OC(O)O$R^x$, —O—$C_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SR, —OCH$_2$OCH$_2$SCH$_3$, —OC(O)NR'$_6$R'$_7$, $C_{1-6}$ alkyl, —(CH$_2$)$_3$C(O)$R^x$, —(CH$_2$)$_3$C(O)O$R^x$, —(CH$_2$)$_3$CN, —OP(O)(OH)$_2$, —OCH$_2$OP(O)(OH$_2$), —OCH$_2$OCH$_2$OP(O)(OH$_2$, —(OCH$_2$)$_n$OC=OCH$_2$NHR$^x$, —(OCH$_2$)$_n$OC(=O)CH$_{(R")}$ NR'$_6$R'$_7$, where n is 0–3, —OCOCH$_2$CH$_2$NH$_3^+$HCOO$^+$, —OCOCH$_2$CH$_2$COOH, —OCO(CH$_2$)$_3$COOH, —OC(O)—Z—C(O)—R', —OC(O)(CH$_2$)$_n$NR$^F$R$^G$ where n is 0–3, or —OC(O)CH$_2$CH$_2$C(O)OCH$_2$CH$_2$OH;

$R^{19}$ is methyl or hydroxymethyl;

$R^x$ is $C_{1-6}$ alkyl, $C_{2-6}$ alkenyl, $C_{2-6}$ alkynyl, $C_{3-6}$ cyclo alkyl any of which groups can be optionally substituted with one to six of the same or different halogen atoms or with one or more hydroxy groups; and $R^W$ is $C_{1-6}$ alkyl any of which groups can be optionally substituted with one to six of the same or different halogen atoms or with one or more hydroxy groups or with one or more carboxy groups or with one or more carboxy $C_{1-6}$ alkyl esters or with one or more mercapto groups.

18. A pharmaceutical formulation comprises an antitumor effective amount of a compound of formula I as claimed in any one of claims 1–16.

19. A method of inhibiting tumor growth in a mammalian host which comprises administering to said mammal a tumor-growth inhibiting amount of a compound of formula I as claimed in any one of claims 1–16.

* * * * *